US010377739B2

(12) United States Patent
Nebolsin et al.

(10) Patent No.: US 10,377,739 B2
(45) Date of Patent: *Aug. 13, 2019

(54) GLUTARIMIDE DERIVATIVES, USE THEREOF, PHARMACEUTICAL COMPOSITION BASED THEREON AND METHODS FOR PRODUCING GLUTARIMIDE DERIVATIVES

(71) Applicant: OBSCHESTVO S OGRANICHENNOI OTVETSTVENNOSTIYU "PHARMENTERPRISES", Moscow (RU)

(72) Inventors: Vladimir Evgenievich Nebolsin, Moskovskaya Obl. (RU); Tatyana Alexandrovna Kromova, Kaluga (RU)

(73) Assignee: OBSCHESTVO S OGRANICHENNOI OTVETSTVENNOSTIYU "PHARMENTERPRISES", Moscow (RU)

( * ) Notice: Subject to any disclaimer, the term of this patent is extended or adjusted under 35 U.S.C. 154(b) by 0 days.

This patent is subject to a terminal disclaimer.

(21) Appl. No.: 16/192,065

(22) Filed: Nov. 15, 2018

(65) Prior Publication Data

US 2019/0084961 A1     Mar. 21, 2019

Related U.S. Application Data

(63) Continuation of application No. 15/718,274, filed on Sep. 28, 2017, now Pat. No. 10,196,377, which is a continuation of application No. 14/783,911, filed as application No. PCT/RU2014/000264 on Apr. 10, 2014, now Pat. No. 9,815,814.

(30) Foreign Application Priority Data

Apr. 12, 2013  (RU) ................................ 2013116826

(51) Int. Cl.
| C07D 401/06 | (2006.01) |
| C07D 401/14 | (2006.01) |
| C07D 405/06 | (2006.01) |
| C07D 409/06 | (2006.01) |
| C07D 413/06 | (2006.01) |
| C07D 417/06 | (2006.01) |
| C07D 471/04 | (2006.01) |
| C07D 453/02 | (2006.01) |
| C07D 487/04 | (2006.01) |

(52) U.S. Cl.
CPC ......... *C07D 401/06* (2013.01); *C07D 401/14* (2013.01); *C07D 405/06* (2013.01); *C07D 409/06* (2013.01); *C07D 413/06* (2013.01); *C07D 417/06* (2013.01); *C07D 453/02* (2013.01); *C07D 471/04* (2013.01); *C07D 487/04* (2013.01)

(58) Field of Classification Search
CPC ... C07D 401/06; C07D 401/14; C07D 405/06
See application file for complete search history.

(56) References Cited

U.S. PATENT DOCUMENTS

| 3,963,691 A | 6/1976 | Hoffman et al. |
| 9,815,814 B2 * | 11/2017 | Nebolsin ............. C07D 401/14 |
| 2011/0257192 A1 | 10/2011 | Lambert et al. |
| 2012/0157387 A1 | 6/2012 | Tam et al. |
| 2016/0046598 A1 | 2/2016 | Nebolsin et al. |
| 2016/0279114 A1 | 9/2016 | Nebolsin et al. |
| 2018/0016253 A1 | 1/2018 | Nebolsin et al. |
| 2018/0016254 A1 | 1/2018 | Nebolsin et al. |
| 2018/0016255 A1 | 1/2018 | Nebolsin et al. |
| 2018/0016256 A1 | 1/2018 | Nebolsin et al. |

(Continued)

FOREIGN PATENT DOCUMENTS

| JP | S606686 A | 1/1985 |
| JP | 04049552 B2 | 2/2008 |
| RU | 1836365 C | 8/1993 |
| RU | 2278857 C2 | 6/2006 |
| RU | 2337908 C2 | 11/2008 |
| WO | 9706140 A1 | 2/1997 |
| WO | 1999001103 A2 | 1/1999 |
| WO | 9912910 A1 | 3/1999 |
| WO | 2001005765 A1 | 1/2001 |
| WO | 2007000246 A1 | 1/2007 |
| WO | 2007007054 A1 | 1/2007 |

OTHER PUBLICATIONS

1998—(KR) Lee, Jae Yeol et al. Synthesis of Contirmationally restricted analogs of ABT-418, isoxazolo [5,4-g] indolizines and isoxazolo[4,5-a] quinolizines, for the nicotinic acetylcholine receptor ligands. Bulletin of the Korean Chemical Society, 1998, 19(11), pp. 1274-1276 (the abstract0 [on-line} CAS (STN), 130:81441, RN 218784-67-9.

(Continued)

*Primary Examiner* — D Margaret M Seaman
(74) *Attorney, Agent, or Firm* — Banner & Witcoff, Ltd.

(57) ABSTRACT

A compound having the following formula:

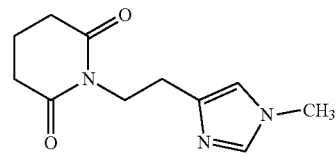

or a pharmaceutically acceptable salt thereof. A medicament or pharmaceutical composition contains the compound. A method of treating a respiratory tract disease includes administering to a patient an effective amount of a compound or a pharmaceutically acceptable salt thereof.

16 Claims, No Drawings

(56) References Cited

U.S. PATENT DOCUMENTS

| | | |
|---|---|---|
| 2018/0016257 A1 | 1/2018 | Nebolsin et al. |
| 2018/0022728 A1* | 1/2018 | Nebolsin .............. C07D 401/14 514/318 |

OTHER PUBLICATIONS

Aug. 4, 2014—Translation of the International Search Report—PCT/RU2014/000264.
2007—Fokkens W.J., Lund V.J., Mullol J. et al., European Position Paper on Rhinosinusitis and Nasal Polyps. Rhinology 2007; 45; 20:1-139.
2005—Falsey AR, Hennessey PA, Formica MA, Cox C, Walsh ??. Respiratory syncytial virus infection in elderly and high-risk adults. N Engl J Med. 2005; 352(17):1749-1759.
Nair H, Nokes DJ, Gessner BD, Dherani M, Madhi SA, Singleton RJ, O'Brien KL, Roca A, Wright PF, Bruce N, Chandran A, Theodoratou E, Sutanto A, Sedyaningsih ER, Ngama M, Munywoki PK, Kartasasmita C, Simoes EA, Rudan I, Weber MW, Campbell H. Global burden of acute lower respiratory infections due to respiratory syncytial virus in young children: a systematic review and meta-analysis. Lancet; 375: 1545-55.
2002—Schauer U, Hoffjan S, Bittscheidt J, Kochling A, Hemmis S, Bongartz S, Stephan V. RSV bronchiolitis and risk of wheeze and allergic sensitisation in the first year of life. Eur Respir J 2002; 20: 1277-83.
2005—Sigurs N, Gustafsson PM, Bjamason R, Lundberg F, Schmidt S, Sigurbergsson F, Kjellman B. Severe respiratory syncytial virus bronchiolitis in infancy and asthma and allergy at age 13. Am J Respir Crit Care Med 2005; 171: 137-41.
2003—Ainhoa Ardeo et al, A practical approach to the fused P-carboline system. Asymmetric synthesis of indolo[2,3-a] Indolizidinones via a diastereoselective intramolecular a-amidoalkylation reaction. /Tetrahedron Letters. 2003. 44. 8445-8448.
2009—Palmenberg, A.; Spiro, D; Kuzmickas, R; Wang, S; Djikeng, A; Rathe, JA; Fraser-Liggett, CM; Liggett, SB (2009)."Sequencing and Analyses of All Known Human rhinovirus Genomes Reveals Structure and Evolution". Science 324 (5923): 55-9. doi:10.1126/science. 1165557. PM1D 19213880.
2010—Storey S. Respiratory syncytial virus market. Nat Rev Drug Discov 2010; 9: 15-6.
1968—Weigand-Hilgetag, Experimental Methods in Organic Chemistry [Russian translation], (N. N. Suvorov, ed.), Moscow, Khimiya, 1968; p. 446.
1994—Yong Sup Lee et al., Studies on the site-selective N-acyliminium ion cyclazation: synthesis of (±)-glochidine and (±)-glochidicine. Heterocycles. vol. 37. No. 1. 1994.
2007—Shimotori et al, Asymmetric synthesis of 5-lactones with lipase catalyst. Flavour and Fragrance Journal.—2007.—V. 22.—No. 6.—pp. 531-539.
2007—Ito et al; Chemoselective Hydrogenation of Imides Catalyzed by CpRu(PN) Complexes and Its Application to the Asymmetric Synthesis of Paroxetine. // Journal of the American Chemical Society.—2007.—V. 129.—No. 2.—pp. 290-291.
1990—Polniaszek, et al; Stereoselective nucleophilic additions to the carbon-nitrogen double bond. 3. Chiral acyliminium ions. // Journal of Organic Chemistry.—1990.—V. 55.—No. 1.—pp. 215-223.

1998—Tanis, Steven P et al. Furan-terminated N-acyliminium ion initiated cyclizations in alkaloid synthesis. Journal of Organic Chemistry, 1998, 63(20), pp. 6914-6928 (the abstract) [on-line] CAS (STN), 129:302741, RN 214462-74-5, 214462-87-0,214462-99-4, 214463-07-7.
1989—Meth-Cohn, Otto et al. A Thiophene analog of praziquantel, and related systems, by intramolecular cyclization of acyliminium salts. Journal of Chemical Reseach, Synopses (5), 1989, pp. 124-125 (abstract) [on-line] CAS (STN), 112:77137, RN 125140-65-0, 125140-66-1.
1984—Kobayashi, Michihiro et al. Sudies on the synthesis of antiulcer agents. Yakugaku Zasshi, 1984, 104(6), pp. 652-658 (abstract) [on-line] CAS (STN), 101 :230442, RN 93447-71-3.
Battler, H.J.—Effects of partially cyclic and ring-methylated nikethamide analogs. Part 2: structure-activity relations in analeptic agents of the nikethamide type.
2014 Copyright—RN 1815-91-4 CA.
Kormendy, Karoly; Ruff, Ferenc; Kovesdi, Istvan (Dep. Org. Chem., Eotvos Lorand Univ., Budapest, H-1088, Hung.). Aminophthalazinone derivatives. XII. Methods for the synthesis of imidazo [2,1-a] phthalazine and pyrimido [2,1-a] phthalazine ring systems. II. Thermal transformation of ([(acyloxy)alkyl] amino)phthalazinones.
Abdel-Gawad, M.; El-Telbany, F.A.; El-Mowafi, H.M.; El-Zanfally, S.; Khalifa, M. (Fac. Pharm., Cairo Univ., Cairo, Egypt). Synthesis and N-alkylation of certain carbon-substituted glutarimides.
1964—Morrison, Glenn C., Cetenko, Wiaczeslaw; Shavel, John, Jr.(Warner Lambert Res. Inst., Morris Plains, NJ). Bischler-Napieralski cyclization of an imide.
RN 95859-86-2 CA.
Imming, Peter, "Synthesis of the First Penicillin Derivatives with Medium-Sized Lactam Ring and of Related Thiazolidines", Arch Pharm, vol. 328, pp. 207-215 (1995).
Greinwald, Roland, et al, "A survey of alkaloids in the genus Lamprolobium Benth", abstract only of Biochecmical Systematics and Ecology 21(3), pp. 405-411, 1993.
Akiyama, Shigeaki, et al., "Preparation of pyrazole compounds and plant disease control agent", abstract only of WO9912910, 1999.
Gesson, J.P., et al. "A practical Method for N-alkylation of succinimide and glutarimide", abstract only of Bulletin de la Societe Chimique de France 129(3), pp. 227-231, 1992.
Abrahm, Thomas et al., "Preparation of heterocyclic amides, in particular arolanes and pyridines as Phosphodiasterase IV (PDE4) inhibitors for the treatment of inflammatory and allergic disorders".
Van der Meer et al., "Erythropoietin in cardiovascular diseases," European Heart Journal (2004) vol. 25, pp. 285-291.
Rakes et al., "Rhonovirus and Respiratory Syncytial Virus in Wheezing Children Requiring Emergency Care," American Journal Respiratory and Critical Care Medicine, 1999, vol. 159, pp. 785-790.
U.S. Appl. No. 14/783,911, filed Oct. 12, 2015, Grandparent.
U.S. Appl. No. 15/718,207, filed Sep. 28, 2017, Related.
U.S. Appl. No. 15/718,226, filed Sep. 28, 2017, Related.
U.S. Appl. No. 15/718,252, filed Sep. 28, 2017, Related.
U.S. Appl. No. 15/718,274, filed Sep. 28, 2017, Parent.
U.S. Appl. No. 15/718,295, filed Sep. 28, 2017, Related.
U.S. Appl. No. 15/718,316, filed Sep. 28, 2017, Related.

* cited by examiner

GLUTARIMIDE DERIVATIVES, USE THEREOF, PHARMACEUTICAL COMPOSITION BASED THEREON AND METHODS FOR PRODUCING GLUTARIMIDE DERIVATIVES

CROSS-REFERENCE TO RELATED APPLICATIONS

This application is a continuation of U.S. application Ser. No. 15/718,274 filed Sep. 28, 2017, now allowed, which is a continuation of U.S. application Ser. No. 14/783,911 filed Oct. 12, 2015, now U.S. Pat. No. 9,815,814, which is a U.S. National Stage application under 35 U.S.C. § 371 of International Application PCT/RU2014/000264 (published as WO 2014/168522 A1), filed Apr. 10, 2014, which claims priority to Application RU 2013116826, filed Apr. 12, 2013. Benefit of the filing date of each of these prior applications is hereby claimed. Each of these prior applications is hereby incorporated by reference in its entirety.

FIELD

The invention relates to novel biologically active compounds, in particular to glutarimide derivatives or pharmaceutically acceptable salt thereof, to use thereof as agents for the prevention and treatment of upper respiratory tract diseases, and to methods for preparing said compounds.

BACKGROUND

Upper respiratory tract chronic diseases are the most common diseases in children and adults throughout the world. The upper respiratory tract chronic diseases include, in particular, rhinosinusitis.

Rhinosinusitis is an inflammation of the mucous tunic of the nose and paranasal sinuses (PNS) and is the most actual problem in the otorhinoryngology (Fokkens W. J., Lund V. J., Mullol J. et al., European Position Paper on Rhinosinusitis and Nasal Polyps. Rhinology 2007; 45; 20:1-139). A cause of rhinosinusitis almost always is mucous congestion, blockage of natural ostia of the PNS, and a disturbance in their ventilation when the mechanism of mucociliary clearance suffers since said mechanism is an important primary innate mechanism protecting the respiratory tract from damaging action of inhaled pollutions, allergens and causal organisms.

Acute rhinosinusitis is a frequent complication of an acute respiratory viral infection (ARVI).

Today, the rhinosinusitis therapy starts with administration of corticosteroids since they have a pronounced anti-inflammatory effect. Corticosteroids are used as monotherapy or in combination with antibiotics. More severe forms of rhinosinusitis require the use of antibiotics. Main corticosteroids are fluticasone, budesonide and mometasone. In the treatment of rhinosinusitis, corticosteroids are prescribed for long-term use, which may cause side effects and tolerance. Side effects are, as a rule, the manifestation of the intrinsic glucocorticosteroid action of these medicaments but in a degree that exceeds the physiological norm.

The prescribed antibiotics are, in general, penicillin antibiotics (amoxicillin, penicillin V) or non-penicillin antibiotics (macrolides, tetracycline) (Fokkens W. J., Lund V. J., Mullol J. et al., European Position Paper on Rhinosinusitis and Nasal Polyps. Rhinology 2007; 45; 20:1-139).

Thus, there is a need for novel preparations that would intensify the treatment of rhinosinusitis and weaken an inflammatory reaction while reducing suppurative inflammation and subsurface injuries in the form of necrotic defects, and would prevent the disease from becoming chronic. Thus, the objective of the present invention is to develop and introduce into practice novel medicaments for the treatment of rhinosinusitis.

Viral infections are a serious health problem. There are no developed antiviral drugs against most hazardous and dangerous viral infections, and the existing medicaments are often toxic to humans or insufficiently effective. Most of existing or under-development drugs act through a specific interaction with specific viral proteins. Such drugs have a limited spectrum of action and promote a rapid emergence of resistant viral variants. Classes IV and V of the Baltimore virus classification system include viruses containing single-stranded (+) or (−) RNA. Class IV includes representatives of the Enterovirus genus of the Picornaviridae family and the Coronaviridae family, and class V includes a respiratory syncytial virus (RSV) of the Paramyxoviridae family and influenza virus of the Orthomyxoviridae family.

The recited groups of viruses have developed an effective strategy of inhibiting the cellular antiviral program. Such aggressive strategy of inhibiting the system of the cellular antiviral protection leads to a high contagiousness and a high pathogenicity of these groups of viruses, which fact is confirmed by the list of diseases caused by the viruses belonging to the Enterovirus genus (poliomyelitis, viral rhinitis (rhinoviral cold)). Today, among viruses of the Enterovirus genus, human rhinoviruses cause the biggest problem. Rhinoviruses, which are replicated in the nasopharyngeal mucosal cells, are a causative agent of upper respiratory tract diseases in humans. Rhinoviruses are causative agents of at least 80% of cold-related diseases. Apart from the enormous economic damage (20 million humans/hour annually in the U.S.), rhinovirus infections cause a large number of complications such as sinusitis and otitis media and are frequently detected in virological examination of children with pneumonia. In asthmatic children, rhinovirus infection is also a cause of acerbations in 80% cases. In adults, rhinovirus may cause exacerbations of both asthma and chronic obstructive pulmonary disease, chronic bronchitis, and mucoviscidosis. Rhinovirus was isolated in pneumonia patients with immunodeficiency conditions.

Since there are more than 100 antigenic types of rhinovirus, this makes it impossible to develop an effective vaccine (Palmenberg, A. C; Spiro, D; Kuzmickas, R; Wang, S; Djikeng, A; Rathe, J A; Fraser-Liggett, C M; Liggett, S B (2009). "Sequencing and Analyses of All Known Human rhinovirus Genomes Reveals Structure and Evolution". Science 324 (5923): 55-9. doi:10.1126/science. 1165557. PM1D 19213880). In addition, there is no an effective chemotherapeutic agent for the treatment of rhinovirus infection.

Coxsackie virus infection (HCXV) is a large group of diseases characterized by pronounced clinical polymorphism. Coxsackie virus infection can manifest itself in meningitis, paralysis, acute respiratory disorders, pneumonia, haemorrhagic conjunctivitis, myocarditis, hepatitis, diabetes and other syndromes. According to the modern classification of viruses, human enteroviruses belonging to the Enterovirus genus are divided into 5 species: 1) poliovirus; 2) human enteroviruses A; 3) human enteroviruses B; 4) human enteroviruses C; and 5) human enteroviruses D. Various serotypes of Coxsackie virus belong to the following enterovirus species: Human enterovirus A (Coxsackie viruses A2-8, 10, 12, 14, and 16); Human enterovirus B (Coxsackie viruses A9, B1-6); Human enterovirus C (Coxsackie viruses A1, 11, 13, 15, 17-22, and 24).

Coxsackie viruses, like other human enteroviruses, are ubiquitous throughout the world. In the temperate countries, their maximum circulation is observed in the summer-autumn season. The viruses are characterized by a high invasiveness, thus promoting their rapid spread in the human population. Coxsackie viruses are often the cause of "sudden" outbreaks in organized children's groups and hospitals; interfamilial spread of the infection occurs as well. A high variability of the viral genome plays an important role in the epidemiology of Coxsackie virus and other enterovirus infections. As a consequence, various serotypes are able to cause different pathology in certain circumstances. On the other hand, the same clinical syndrome may be caused by different serotypes and different enterovirus species. Genetic variability, selection and rapid spread of modified viruses result in large-scale outbreaks of the diseases, the etiology of which has no relation to these viruses, or their circulation was not recorded for a long time.

The primary replication of Coxsackie virus occurs in the nasopharynx- and gut-associated lymphoid tissue. It causes local lesions expressed in the symptoms of ARD, herpangina, pharyngitis, etc. In the throat the virus is detected until the seventh day, and is excreted with faeces for 3-4 weeks (in case of immunodeficiency for several years). Viremia, as a result of which the virus penetrates the target organs, follows the primary replication of the virus. For Coxsackie viruses such target organs may be the brain and spinal cord, meninges, upper respiratory tract, lungs, heart, liver, skin, etc. Coxsackie virus B can cause severe generalized pathological processes in newborns, resulting in necrosis in the heart, brain and spinal cord, liver and kidneys. The viruses cause the following clinic syndromes: aseptic meningitis (Coxsackie viruses A2, 3, 4, 6, 7, 9, 10, and B1-6); acute systemic disease in children with myocarditis and meningoencephalitis (Coxsackie viruses D1-5); paralysis (Coxsackie viruses A1, 2, 5, 7, 8, 9, 21, and B2-5); herpangina (Coxsackie viruses A2, 3, 4, 5, 6, 8, and 10); acute pharyngitis (Coxsackie viruses A10, 21); contagious rhinitis (Coxsackie viruses A21, 24); damage of the upper respiratory tract (Coxsackie viruses A9, 16, and B2-5) (16); pericarditis, myocarditis (Coxsackie viruses B1-5); hepatitis (Coxsackie viruses A4, 9, 20, and B5); diarrhea of newborns and infants (Coxsackie viruses A18, 20, 21, 24); acute haemorrhagic conjunctivitis (Coxsackie viruses A24); Hand, Foot and Mouth Disease (Coxsackie viruses A5, 10, 16); exanthemata (Coxsackie viruses A4, 5, 6, 9, 16); pleurodynia (Coxsackie viruses B3, 5); rash (Coxsackie viruses B5); fever (Coxsackie viruses B1-6); There are absent specific chemotherapeutic agents for the treatment of Coxsackie virus infections. Pathogenic and symptomatic therapy is applied, depending on the clinical form of the disease.

The Paramyxoviridae family includes the representatives of the genus Respirovirus (human parainfluenza virus types 1, 2, 3, 4, and 5) and genus Pneumovirus (respiratory-syncytial virus).

Paramyxoviruses are an important class of viruses that are associated with respiratory diseases. Respiratory-syncytial virus (RSV) is known to be a dominant pathogen of the lower respiratory tract throughout the world.

RSV is a pathogen in newborns and infants and is a causative agent of at least 70% of severe viral bronchitis and/or pneumonias, the majority part of which is characterized by wheezing and dyspnea. These bronchiolites are the most common cause of hospitalization in the winter season during the first year of child's life. RSV also causes bronchiolitis, pneumonia and chronic obstructive respiratory disease in humans of all-ages and makes a significant contribution to an excess mortality in the winter season.

In infants and young children, RSV is the main inducer of rales and exacerbations of asthma. RSV-infected adults are reported to have an increased risk of exacerbations of asthma leading to hospitalization, relative to health patients (Falsey A R, Hennessey P A, Formica M A, Cox C, Walsh E E. Respiratory syncytial virus infection in elderly and high-risk adults. N Engl J Med. 2005; 352(17):1749-1759).

RSV takes a leading position on the number of fatal cases among viral infections. Only the U.S. spends $2.4 billion on the treatment of viral lower respiratory tract diseases in children. By one year of age, 50-65% of children have been infected with this virus, and by two years of age, almost 100% of children have been infected. In addition to premature newborns and older persons, a high-risk group includes persons with diseases of the cardiovascular, respiratory and immune systems. Based on published and non-published data, it has been calculated that RSV causes in the world 33.8 millions of cases of episodic acute lower respiratory tract infections (LRTI), 3.4 millions of severe LRTI cases requiring hospitalization, and 66,000-99,000 of fatal cases among children under the age of 5 (Nair H, Nokes D J, Gessner B D, Dherani M, Madhi S A, Singleton R J, O'Brien K L, Roca A, Wright P F, Bruce N, Chandran A, Theodoratou E, Sutanto A, Sedyaningsih E R, Ngama M, Munywoki P K, Kartasasmita C, Simoes E A, Rudan I, Weber M W, Campbell H. Global burden of acute lower respiratory infections due to respiratory syncytial virus in young children: a systematic review and meta-analysis. Lancet; 375: 1545-55). Only in the U.S., 90,000 premature newborns, 125,000 hospitalized newborns, more than 3.5 million children under the age of 2, and 175,000 hospitalized adults need the treatment every year (Storey S. Respiratory syncytial virus market. Nat Rev Drug Discov 2010; 9: 15-6.). In 1 year of age, about a third of children hospitalized with acute bronchiolitis have an episodic dyspnea and an increased sensitivity to common allergens (Schauer U, Hoffjan S, Bittscheidt J, Kochling A, Hemmis S, Bongartz S, Stephan V. RSV bronchiolitis and risk of wheeze and allergic sensitisation in the first year of life. Eur Respir J 2002; 20: 1277-83). These symptoms may return in following years (Sigurs N, Gustafsson P M, Bjarnason R, Lundberg F, Schmidt S, Sigurbergsson F, Kjellman B. Severe respiratory syncytial virus bronchiolitis in infancy and asthma and allergy at age 13. Am J Respir Crit Care Med 2005; 171: 137-41). Bronchiolitis may also be caused by rhinovirus, coronovirus, influenza and parainfluenza viruses, and adenovirus. However, among the all recited viruses, RSV is the most frequent cause of hospitalization due to bronchiolitis. An adaptive immunity formed as a result of a past RSV infection both in children (with an immature immune system) and in adults are short-term and does not provide a complete antiviral protection. This fact leads to reinfections occurred throughout life. In first months of life, the blood of newborns comprises maternal anti-RSV antibodies; however, they do not protect a child.

It should be noted that the only chemotherapeutic agent exerting some beneficial effects in infections caused by (+) and (−) RNA viruses is ribavirin. However, ribavirin is a relatively toxic drug frequently causing anemia. Its main feature is a long-term storage in red blood cells. As a result, traces of ribavirin are detected even 6 months after the end of therapy. Also, there are reports about teratogenicity of ribavirin.

Influenza virus belongs to the Orthomyxoviridae family comprising four genera: influenza viruses A, B, and C and thogotoviruses (sometimes referred to as influenza D virus). Humans can be infected by influenza viruses A, B and C, but only type A causes pandemics posing a serious threat for humans. According to the WHO data, influenza causes 3-5 million cases of severe diseases and 250,000 to 500,000 fatal cases every year throughout the world.

Influenza virus is also exhaled by patients with exacerbations of asthma; however, the number of cases is 1-9% of other viruses.

Two main surface glycoproteins of influenza virus, hemagglutinin and neuraminidase, are responsible for the virus attachment and the release thereof from a host cell and, at the same time, are the main target for antibodies. Type A viruses are subdivided into subtypes on the basis of different combinations of 16 variants of hemagglutinin and 9 variants of neuraminidase. All known subtypes have been confirmed for wild birds which are considered to be a natural host for influenza type A viruses. Only three subtypes, in particular A (H1N1), A (H2N2) and A (H3N2), are known in the human population. These viruses together with influenza type B viruses are responsible for annual epidemics of various severities. The diversity of influenza viruses is a genetically determined feature. The segmented negative-sense RNA genome organization of influenza virus facilitates the exchange of genomic segments (so-called re-assortment) between different strains during mixed infection. In addition, the lack of proofreading activity in the polymerase of influenza virus leads to a high mutation rate in the virus genes, thus leading to regular appearance of influenza strains with "new" antigenic properties. If the change is sufficient to overcome the pre-existing immunity in the human population, the virus is capable of causing an epidemic. When the human population is completely naive to a newly emerging variant, the virus can readily cause infection and be transmitted from infected to uninfected persons, and cause a pandemic. The above-indicated peculiarities determine difficulties in the creation of anti-influenza vaccines. There are known two classes of the medicaments inhibiting the M2 protein or neuraminidase of influenza virus. Adamantane derivatives (amantadine and rimantadine) are active against influenza type A viruses (but not against type B). The neurominidase-inhibiting medicaments are zanamivir and oseltamivir. Both medicaments are preferably effective at the early stage.

The most common method for synthesis of dicarboxylic acid imides is a method of thermal cyclization comprising heating a dicarboxylic acid or a derivative thereof, such as anhydride, diester and the like, with a primary amine or an amide thereof. The yield of cyclic imides is usually 80%; however, since the process is conducted under a high temperature, it may be used only for the synthesis of thermally stable imides [Weigand-Hilgetag, Experimental Methods in Organic Chemistry [Russian translation], (N. N. Suvorov, ed.), Moscow, Khimiya, 1968; p. 446].

The article of Yong Sup Lee et al., Studies on the site-selective N-acyliminium ion cyclazation: synthesis of (±)-glochidine and (±)-glochidicine. Heterocycles. Vol 37. No 1. 1994, discloses the preparation of succinimide histamine by fusing histamine dihydrochloride and succinic anhydride under heating of the initial reactants to 200-230° C. for 40 minutes.

The international publication of patent application WO2007/000246 discloses a method for synthesis of gluta-rimides by alkylation of piperidine-2,6-dione and pyrrolidin-2,5-dione with corresponding halo derivatives in DMF, followed by separation of the target substituted imides by preparative chromatography, which is not applicable for the synthesis of macro amounts.

The article of Shimotori et al, Asymmetric synthesis of 5-lactones with lipase catalyst. Flavour and Fragrance Journal.—2007.—V. 22.—No. 6.—pp. 531-539, describes a method for preparing cyclic imides by cyclization of monoamides of corresponding dicarboxylic acids by using a dehydrating agent as a carboxylic group-activating reactant, such as acetic anhydride.

The article of Ito et al; Chemoselective Hydrogenation of Imides Catalyzed by CpRu(PN) Complexes and Its Application to the Asymmetric Synthesis of Paroxetine. // Journal of the American Chemical Society.—2007.—V. 129.—No. 2.—pp. 290-291, describes a method for preparing cyclic imides by cyclization of monoamides of corresponding dicarboxylic acids by using a dehydrating agent as a carboxylic group-activating reactant, such as acetyl chloride.

The article of Polniaszek, et al; Stereoselective nucleophilic additions to the carbon-nitrogen double bond. 3. Chiral acyliminium ions. // Journal of Organic Chemistry.—1990.—V. 55.—No. 1.—pp. 215-223, teaches a method for preparing cyclic imides by cyclization of monoamides of corresponding dicarboxylic acids by using a dehydrating agent as a carboxylic group-activating reactant, such as carbonyldiimidazole.

The article of Ainhoa Ardeo et al, A practical approach to the fused P-carboline system. Asymmetric synthesis of indolo[2,3-α]indolizidinones via a diastereoselective intramolecular α-amidoalkylation reaction. /Tetrahedron Letters. 2003. 44. 8445-8448, discloses a method for preparing cyclic imides from a primary amine and a corresponding anhydride, wherein a dehydrating agent is an excess of glutaric or succinic anhydride. In particular, said article provides a scheme of the synthesis of glutarimidotryptamine and succinimidotryptamine from tryptamine and anhydride of a corresponding acid under boiling in acetic acid. The yield of glutarimidotryptamine and succinimidotryptamine prepared by said method is 67% and 81%, respectively.

The publication of international application WO 2007/007054 discloses succinimide and glutarimide derivatives of general formula (I) having inhibitory action on DNA methylation in cells, in particular tumor cells. Compounds disclosed in said article are prepared by an addition reaction between an amino derivative comprising a hydrocarbon chain and a corresponding anhydride or acid, or ether, followed by optional cyclization optionally in the presence of a base.

Thus, the objective of the present invention is to provide novel non-toxic glutarimide derivatives which are effective in the treatment of upper respiratory tract diseases.

SUMMARY OF THE INVENTION

The present invention relates to glutarimide derivatives of general formula I:

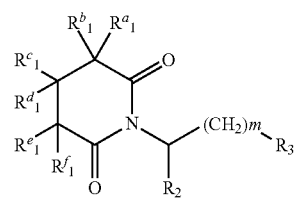

wherein m is an integer from 0 to 2;

$R^a_1$, $R^b_1$, $R^c_1$, $R^d_1$, $R^e_1$, and $R^f_1$, each independently represents hydrogen, $C_1$-$C_6$alkyl; —$NH_2$, —$NHC_1$-$C_6$alkyl, hydroxyl, or $C_1$-$C_6$alkoxy;

$R_2$ is hydrogen, $C_1$-$C_6$alkyl, —C(O)OH, —C(O)O$C_1$-$C_6$alkyl;

$R_3$ is:

1) a 5-membered saturated or unsaturated heterocyclic group comprising from 1 to 4 heteroatoms selected from N, O and S, optionally substituted with 1 to 3 substituents selected from halogen, $C_1$-$C_6$alkyl, $C_1$-$C_6$alkoxy, —C(O)OH, —C(O)O$C_1$-$C_6$alkyl, —NHC(O)$C_1$-$C_6$alkyl, phenyl, or pyridinyl;

2) a 6-membered saturated or unsaturated heterocyclic group comprising from 1 to 2 heteroatoms selected from N and O, optionally substituted with a group selected from halogen and $C_1$-$C_6$alkyl;

3) a 5-membered unsaturated heterocyclic group comprising from 1 to 3 heteroatoms selected from N and S, optionally substituted with 1 or 2 substituents selected from $C_1$-$C_6$alkyl, condensed with a 6-membered unsaturated nitrogen-containing cyclic or heterocyclic group optionally substituted with 1 or 2 substituents selected from hydroxyl, halogen or $C_1$-$C_6$alkyl;

4) a 6-membered unsaturated cyclic or heterocyclic group comprising from 1 to 2 nitrogen atoms, condensed with a 5- or 6-membered unsaturated heterocyclic group comprising from 1 to 3 heteroatoms selected from N and S; or 5) a group of the formula:

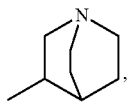

or a pharmaceutically acceptable salt thereof, with a proviso that the compound is not a compound, wherein:

when m is 1, $R^a_1$, $R^b_1$, $R^c_1$, $R^d_1$, $R^e_1$, and $R^f_1$, are hydrogen and $R_2$ is —C(O)OCH$_3$, $R_3$ is not:

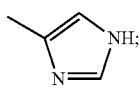

when m is 1, $R^a_1$, $R^b_1$, $R^c_1$, $R^d_1$, $R^e_1$, and $R^f_1$, are hydrogen and $R_2$ is hydrogen, $R_3$ is not:

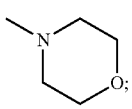

when m is 1, $R^a_1$ is an amino group and $R^a_1$, $R^b_1$, $R^c_1$, $R^d_1$, $R^e_1$, and $R^f_1$ are hydrogen, or $R^e_1$ is an amino group and $R^a_1$, $R^b_1$, $R^c_1$, $R^d_1$, and $R^f_1$ are hydrogen and $R_2$ is hydrogen, $R_3$ is not:

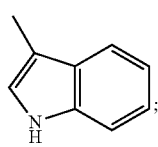

when m is 1, $R^a_1$, $R^b_1$, $R^c_1$, $R^d_1$, $R^e_1$, and $R^f_1$ are hydrogen and $R_2$ is hydrogen, $R_3$ is not:

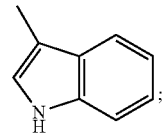

when m is 1, $R^a_1$, $R^b_1$, $R^c_1$, $R^d_1$, $R^e_1$, and $R^f_1$ are hydrogen and $R_2$ is hydrogen, $R_3$ is not:

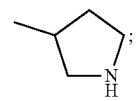

when m is 1, $R^a_1$, $R^b_1$, $R^c_1$, $R^d_1$, $R^e_1$, and $R^f_1$ are hydrogen and $R_2$ is hydrogen, $R_3$ is not:

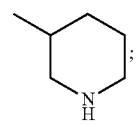

when m is 1, $R^a_1$, $R^b_1$, $R^c_1$, $R^d_1$, $R^e_1$, and $R^f_1$ are hydrogen and $R_2$ is hydrogen, $R_3$ is not:

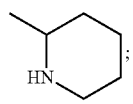

when m is 1, $R^a_1$, $R^b_1$, $R^c_1$, $R^d_1$, $R^e_1$, and $R^f_1$ are hydrogen and $R_2$ is hydrogen, $R_3$ is not:

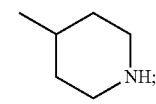

when m is 1, $R^a_1$, $R^b_1$, $R^c_1$, $R^d_1$, $R^e_1$, and $R^f_1$ are hydrogen and $R_2$ is hydrogen, $R_3$ is not:

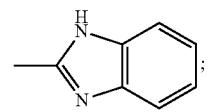

when m is 1, $R^a_1$, $R^b_1$, $R^c_1$, $R^d_1$, $R^e_1$, and $R^f_1$ are hydrogen and $R_2$ is —C(O)OH, $R_3$ is not:

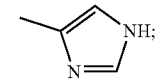

when m is 1, $R^a_1$, $R^b_1$, $R^c_1$, $R^d_1$, $R^e_1$, and $R^f_1$ are hydrogen and $R_2$ is —C(O)OH, $R_3$ is not:

when m is 1, $R^a_1$, $R^b_1$, $R^c_1$, $R^d_1$, $R^e_1$, and $R^f_1$ are hydrogen and $R_2$ is hydrogen, $R_3$ is not:

[3-methylindole structure]

when m is 1, $R^a_1$, $R^b_1$, $R^c_1$, $R^d_1$, $R^e_1$, and $R^f_1$ are hydrogen and $R_2$ is hydrogen, $R_3$ is not:

[2-methylthiophene structure]

when m is 1, $R^a_1$, $R^b_1$, $R^c_1$, $R^d_1$, $R^e_1$, and $R^f_1$ are hydrogen and $R_2$ is hydrogen, $R_3$ is not:

[2-methylfuran structure]

when m is 2, $R^a_1$, $R^b_1$, $R^c_1$, $R^d_1$, $R^e_1$, and $R^f_1$ are hydrogen and $R_2$ is hydrogen, $R_3$ is not:

[2-methylfuran structure]

when m is 2, $R^a_1$, $R^b_1$, $R^c_1$, $R^d_1$, $R^e_1$, and $R^f_1$ are hydrogen and $R_2$ is hydrogen, $R_3$ is not:

[3-methylpyrrole structure]

when m is 1, $R^a_1$, $R^b_1$, $R^c_1$, $R^d_1$, $R^e_1$, and $R^f_1$ are hydrogen and $R_2$ is hydrogen, $R_3$ is not:

[methyl triazole-NH structure]

The present invention also relates to a medicament for the treatment of upper respiratory tract diseases, wherein the medicament is a glutarimide derivative of general formula (I) or a pharmaceutically acceptable salt thereof.

Another object of the present invention is a pharmaceutical composition for the treatment of upper respiratory tract diseases, comprising an effective amount of a glutarimide derivative of general formula (I) or a pharmaceutically acceptable salt thereof, and a pharmaceutically acceptable carrier.

The present invention further relates to a method for treating upper respiratory tract diseases, comprising administering to a patient an effective amount of a glutarimide derivative of general formula (I) or a pharmaceutically acceptable salt thereof.

The present invention also relates to a method for preparing a glutarimide derivative of general formula (I) or a pharmaceutically acceptable salt thereof by heating a dicarboxylic acid monoamide of general formula (II)

Formula II

[structure of dicarboxylic acid monoamide with OH, $R^c_1$, $R^d_1$, $R_2$, NH, $(CH_2)_m$, $R_3$, $R^a_1$, $R^b_1$, $R^e_1$, $R^f_1$ groups]

wherein m is an integer from 0 to 2;

$R^a_1$, $R^b_1$, $R^c_1$, $R^d_1$, $R^e_1$, and $R^f_1$, each independently represents hydrogen, $C_1$-$C_6$alkyl; —$NH_2$, —$NHC_1$-$C_6$alkyl, hydroxyl, or $C_1$-$C_6$alkoxy;

$R_2$ is hydrogen, $C_1$-$C_6$alkyl, —C(O)OH, or —C(O)$C_1$-$C_6$alkyl; $R_3$ is:

1) a 5-membered saturated or unsaturated heterocyclic group comprising from 1 to 4 heteroatoms selected from N, O and S, optionally substituted with 1 to 3 substituents selected from halogen, $C_1$-$C_6$alkyl, $C_1$-$C_6$alkoxy, —C(O)OH, —C(O)O$C_1$-$C_6$alkyl, —NHC(O)$C_1$-C6alkyl, phenyl, or pyridinyl;

2) a 6-membered saturated or unsaturated heterocyclic group comprising from 1 to 2 heteroatoms selected from N and O, optionally substituted with a group selected from halogen and $C_1$-$C_6$alkyl;

3) a 5-membered unsaturated heterocyclic group comprising from 1 to 3 heteroatoms selected from N and S, optionally substituted with 1 or 2 substituents selected from $C_1$-$C_6$alkyl, condensed with a 6-membered unsaturated nitrogen-containing cyclic or heterocyclic group optionally substituted with 1 or 2 substituents selected from hydroxyl, halogen or $C_1$-$C_6$alkyl;

4) a 6-membered unsaturated cyclic or heterocyclic group comprising from 1 to 2 nitrogen atoms, condensed with a 5- or 6-membered unsaturated heterocyclic group comprising from 1 to 3 heteroatoms selected from N and S; or 5) a group of the formula:

[quinuclidine-like bicyclic structure with N]

with a dehydrating agent in an organic solvent.

DETAILED DESCRIPTION OF THE INVENTION

Preferred compounds according to the invention are compounds of general formula I, wherein m is an integer from 0 to 2;

$R^a_1$ and $R^b_1$ are hydrogen, methyl, amino, or hydroxyl;

$R^c_1$ and $R^d_1$ are hydrogen, methyl, amino, or hydroxyl;

$R^e_1$ and $R^f_1$ are hydrogen or methyl;

$R_2$ is hydrogen, methyl, carboxyl, methoxycarbonyl, or ethoxycarbonyl;

a group selected from:

[three imidazole structures: methylimidazole, N-methyl methylimidazole, 2-methylimidazole]

-continued
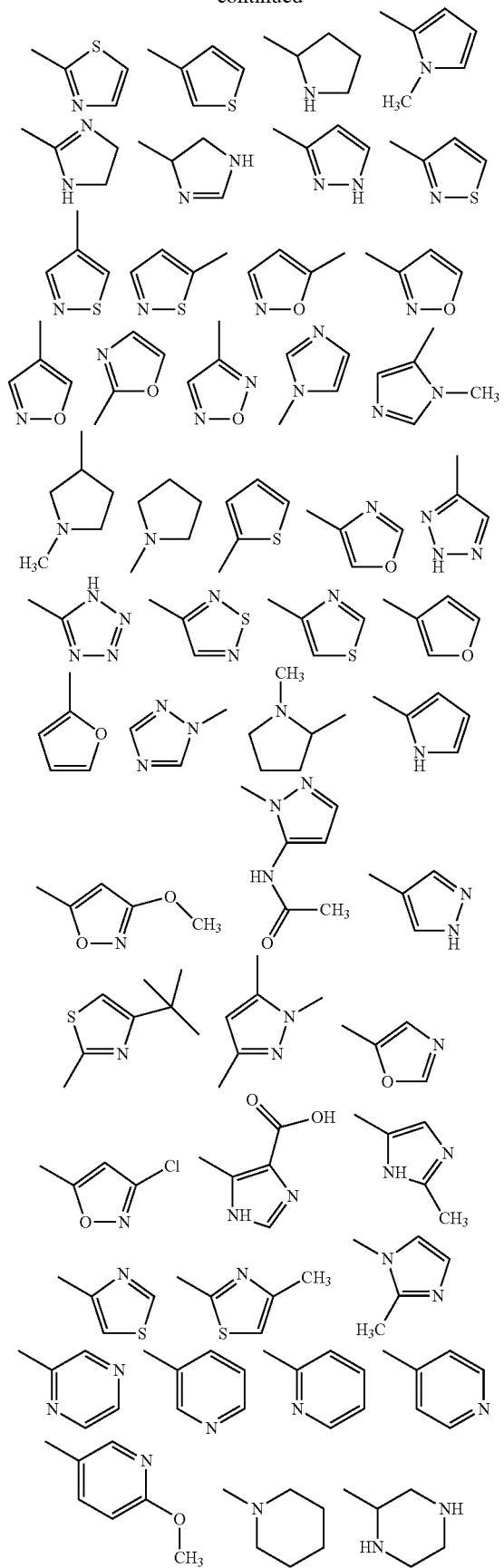
-continued
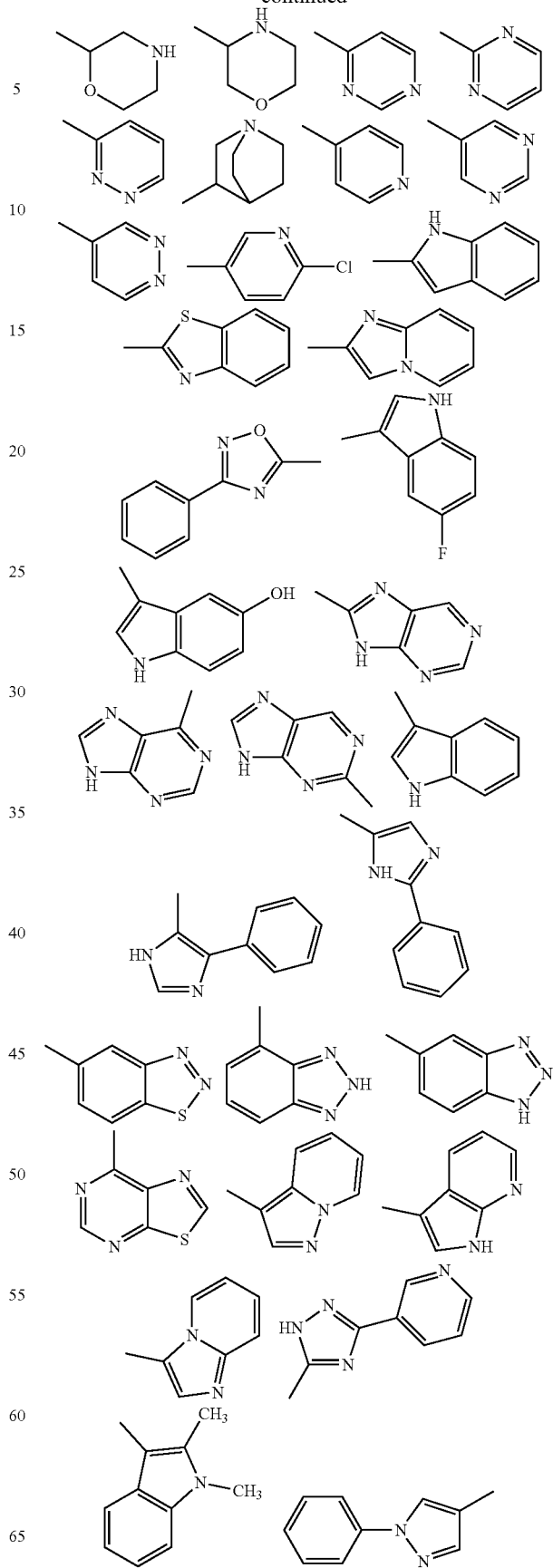

-continued
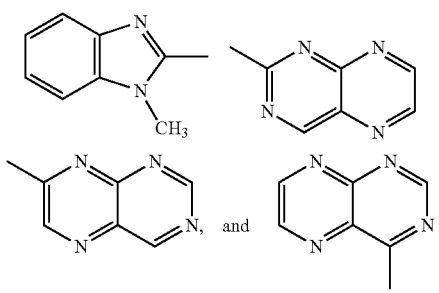
The most preferred compounds according to the present invention are compounds represented in Table 1.
TABLE 1
| Number of a compound | Structure |
|---|---|
| 1 | (structure) |
| 2 | (structure) |
| 3 | (structure) |
| 4 | (structure) |
| 5 | (structure) |
| 6 | (structure) |
TABLE 1-continued
| Number of a compound | Structure |
|---|---|
| 7 | (structure) |
| 8 | (structure) |
| 9 | (structure) |
| 10 | (structure) |
| 11 | (structure) |
| 12 | (structure) |
| 13 | (structure) |
| 14 | (structure) |

TABLE 1-continued

| Number of a compound | Structure |
| --- | --- |
| 15 | 2,6-dioxopiperidin-1-yl ethyl linked to 5-hydroxyindole |
| 16 | 2,6-dioxopiperidin-1-yl ethyl linked to 4,5-dihydro-1H-imidazol-2-yl |
| 17 | 2,6-dioxopiperidin-1-yl ethyl linked to isothiazol-5-yl |
| 18 | 2,6-dioxopiperidin-1-yl ethyl linked to oxazol-2-yl |
| 19 | 2,6-dioxopiperidin-1-yl ethyl linked to 1,2,5-oxadiazol-3-yl |
| 20 | 3,3-dimethyl-2,6-dioxopiperidin-1-yl ethyl linked to 1H-imidazol-4-yl |
| 21 | 2,6-dioxopiperidin-1-yl, methyl ester of tryptophan derivative |
| 22 | 2,6-dioxopiperidin-1-yl ethyl linked to 1-methylpyrrolidin-3-yl |
| 23 | 2,6-dioxopiperidin-1-yl ethyl linked to pyrrolidin-1-yl |
| 24 | 2,6-dioxopiperidin-1-yl propyl linked to 1H-imidazol-1-yl |
| 25 | 2,6-dioxopiperidin-1-yl ethyl linked to 1-methyl-1H-imidazol-5-yl |
| 26 | 2,6-dioxopiperidin-1-yl, ethyl ester of histidine derivative |
| 27 | 2,6-dioxopiperidin-1-yl, ethyl ester of tryptophan derivative |
| 28 | 4-hydroxy-2,6-dioxopiperidin-1-yl ethyl linked to 1H-imidazol-4-yl |
| 29 | 3-hydroxy-2,6-dioxopiperidin-1-yl ethyl linked to 1H-imidazol-4-yl |
| 30 | 2,6-dioxopiperidin-1-yl ethyl linked to 1H-imidazol-1-yl |

TABLE 1-continued
| Number of a compound | Structure |
|---|---|
| 31 | 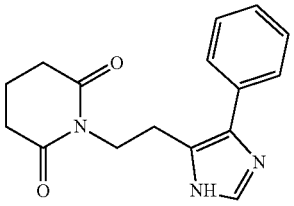 [SMILES: O=C1CCCC(=O)N1CCc1[nH]cnc1-c1ccccc1] |
| 32 | 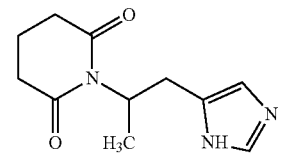 [SMILES: CC(Cc1cnc[nH]1)N1C(=O)CCCC1=O] |
| 33 | 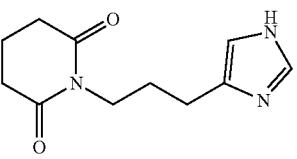 [SMILES: O=C1CCCC(=O)N1CCCc1c[nH]cn1] |
| 34 | 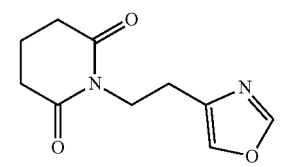 [SMILES: O=C1CCCC(=O)N1CCc1cocn1] |
| 35 | 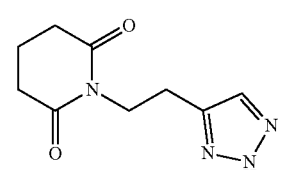 |
| 36 | 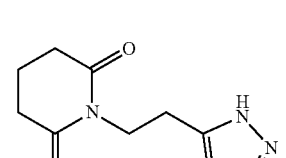 |
| 37 | 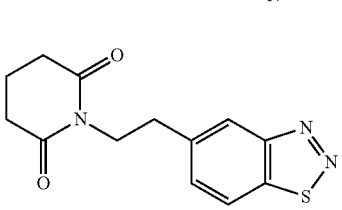 |
| 38 | 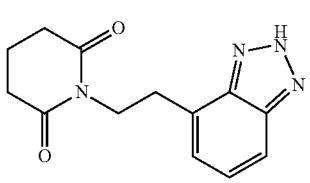 [SMILES: O=C1CCCC(=O)N1CCc1cccc2n[nH]nc12] |
| 39 | 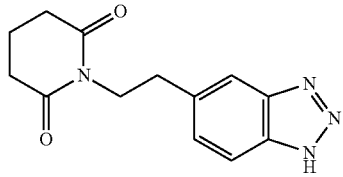 [SMILES: O=C1CCCC(=O)N1CCc1ccc2[nH]nnc2c1] |
| 40 | 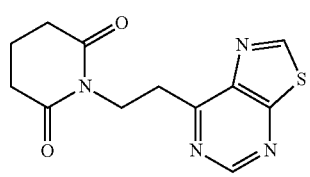 [SMILES: O=C1CCCC(=O)N1CCc1ncnc2scnc12] |
| 41 | 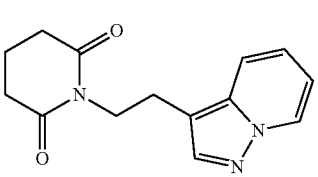 [SMILES: O=C1CCCC(=O)N1CCc1cnn2ccccc12] |
| 42 | 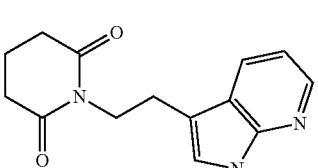 |
| 43 | 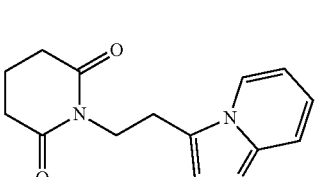 |
| 44 | 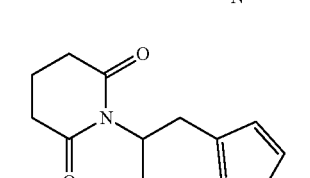 |
| 45 | 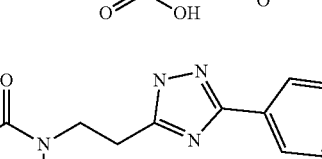 |
| 46 | 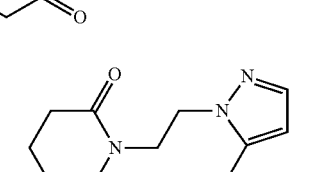 |

TABLE 1-continued

| Number of a compound | Structure |
|---|---|
| 47 | 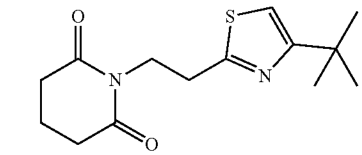 [SMILES: CC(C)(C)c1csc(CCN2C(=O)CCCC2=O)n1] |
| 48 | 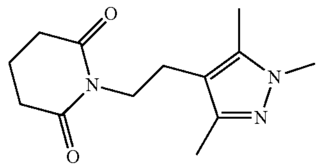 [SMILES: Cc1nn(C)c(C)c1CCN1C(=O)CCCC1=O] |
| 49 | 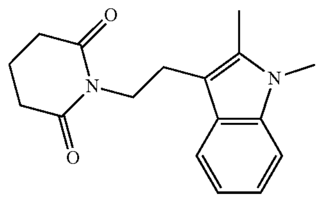 [SMILES: Cc1c(CCN2C(=O)CCCC2=O)c2ccccc2n1C] |
| 50 | 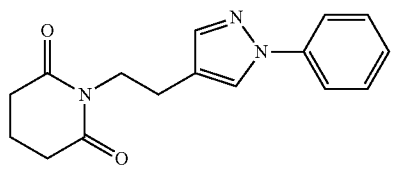 [SMILES: O=C1CCCC(=O)N1CCc1cnn(-c2ccccc2)c1] |
| 51 | 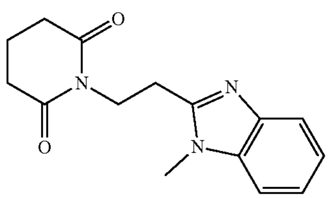 [SMILES: Cn1c(CCN2C(=O)CCCC2=O)nc2ccccc21] |
| 52 | 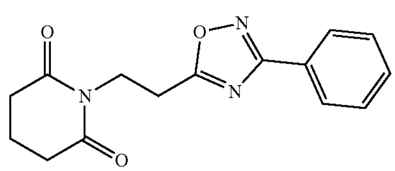 [SMILES: O=C1CCCC(=O)N1CCc1nc(-c2ccccc2)no1] |
| 53 | 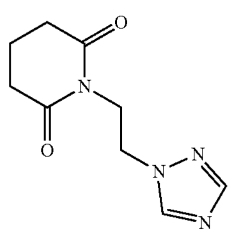 [SMILES: O=C1CCCC(=O)N1CCn1cncn1] |
| 54 | 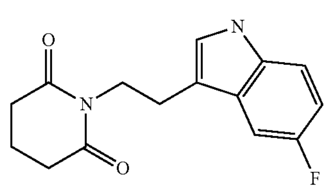 [SMILES: O=C1CCCC(=O)N1CCc1c[nH]c2ccc(F)cc12] |

TABLE 1-continued

| Number of a compound | Structure |
|---|---|
| 55 | 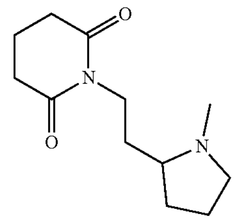 [SMILES: CN1CCCC1CCN1C(=O)CCCC1=O] |
| 56 | 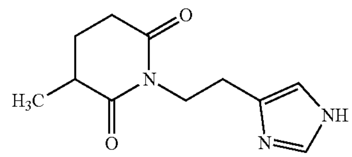 [SMILES: CC1CCC(=O)N(CCc2c[nH]cn2)C1=O] |
| 57 | 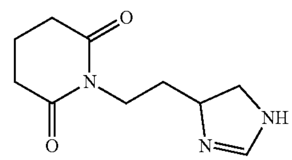 [SMILES: O=C1CCCC(=O)N1CCC1CNC=N1] |
| 58 | 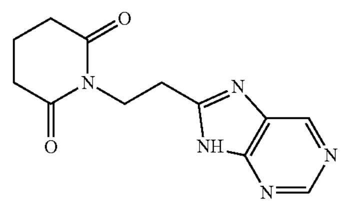 [SMILES: O=C1CCCC(=O)N1CCc1nc2cncnc2[nH]1] |
| 59 | 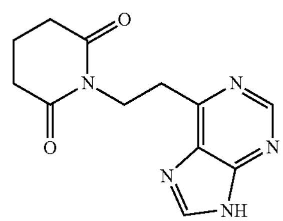 [SMILES: O=C1CCCC(=O)N1CCc1ncnc2[nH]cnc12] |
| 60 | 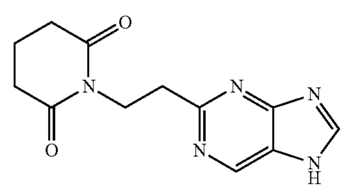 [SMILES: O=C1CCCC(=O)N1CCc1ncc2[nH]cnc2n1] |
| 61 | 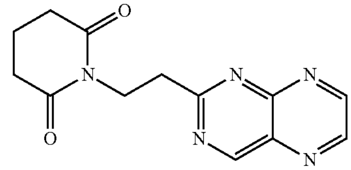 [SMILES: O=C1CCCC(=O)N1CCc1ncc2nccnc2n1] |
| 62 | 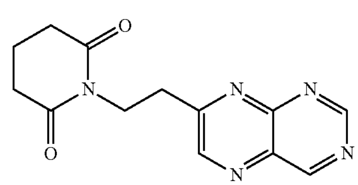 [SMILES: O=C1CCCC(=O)N1CCc1cnc2cncnc2n1] |

TABLE 1-continued

| Number of a compound | Structure |
|---|---|
| 63 | 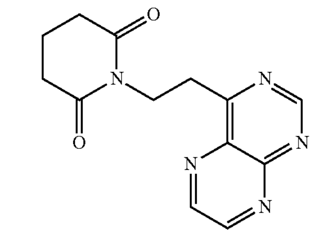 [SMILES: O=C1CCCC(=O)N1CCc1ncnc2nccnc12] |
| 64 | 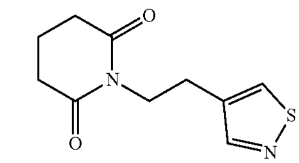 [SMILES: O=C1CCCC(=O)N1CCc1cnsc1] |
| 65 | 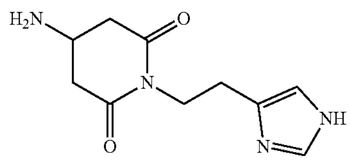 [SMILES: NC1CC(=O)N(CCc2c[nH]cn2)C(=O)C1] |
| 66 | 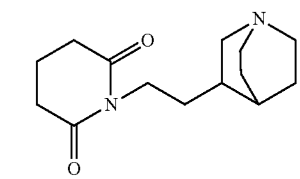 [SMILES: O=C1CCCC(=O)N1CCC1CN2CCC1CC2] |
| 67 | 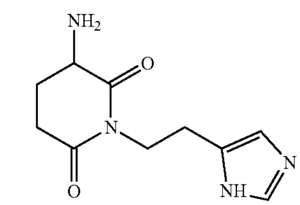 [SMILES: NC1CCC(=O)N(CCc2cnc[nH]2)C1=O] |
| 68 | 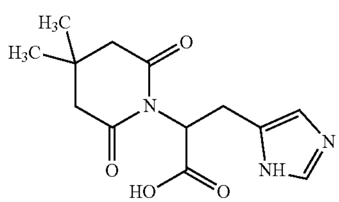 [SMILES: CC1(C)CC(=O)N(C(Cc2cnc[nH]2)C(=O)O)C(=O)C1] |
| 69 | 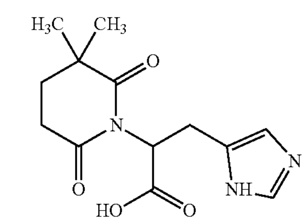 [SMILES: CC1(C)CCC(=O)N(C(Cc2cnc[nH]2)C(=O)O)C1=O] |
| 70 | 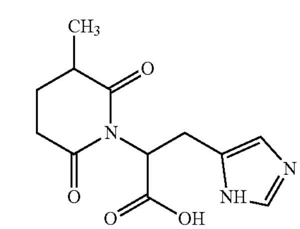 [SMILES: CC1CCC(=O)N(C(Cc2cnc[nH]2)C(=O)O)C1=O] |
| 71 | |
| 72 | |
| 73 | |
| 74 | |
| 75 | |
| 76 | |
| 77 | |

TABLE 1-continued
| Number of a compound | Structure |
|---|---|
| 78 | 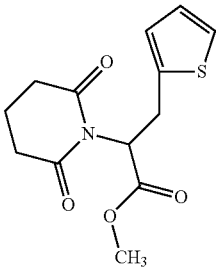 |
| 79 | 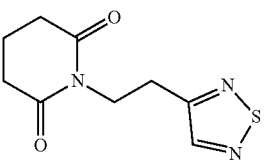 [SMILES: O=C1CCCC(=O)N1CCc1cnsn1] |
| 80 | 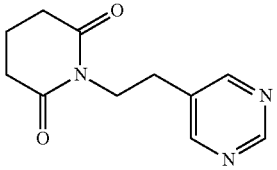 [SMILES: O=C1CCCC(=O)N1CCc1cncnc1] |
| 81 | 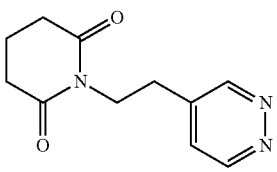 |
| 82 | 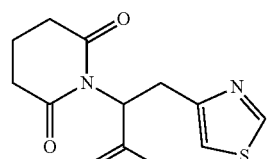 |
| 83 | 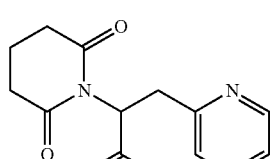 |
| 84 | 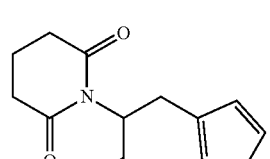 |
| 85 | 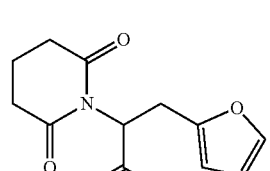 |
| 86 | 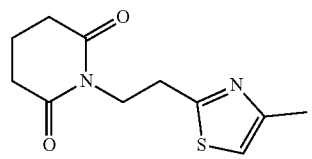 [SMILES: Cc1csc(CCN2C(=O)CCCC2=O)n1] |
| 87 | 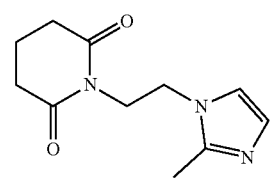 [SMILES: Cc1nccn1CCN1C(=O)CCCC1=O] |
| 88 | 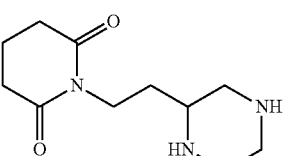 |
| 89 | 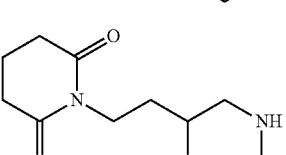 |
| 90 | 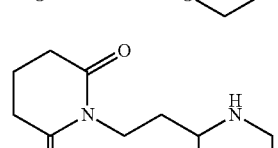 |
| 91 | 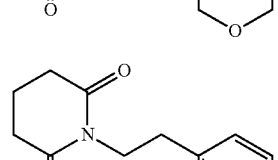 |
| 92 | 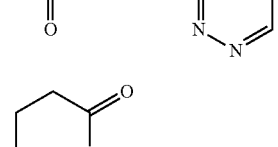 |
| 93 | 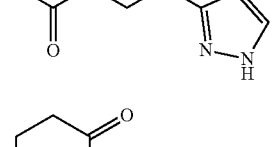 |
| 94 | 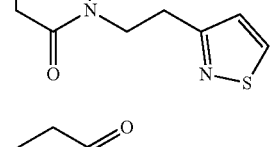 |

TABLE 1-continued

| Number of a compound | Structure |
|---|---|
| 95 | N-(2-(isoxazol-4-yl)ethyl)piperidine-2,6-dione |
| 96 | N-(2-(isoxazol-5-yl)ethyl)piperidine-2,6-dione |
| 97 | N-(2-(pyrimidin-4-yl)ethyl)piperidine-2,6-dione |
| 98 | N-(2-(pyrimidin-2-yl)ethyl)piperidine-2,6-dione |
| 99 | N-(2-(1H-pyrrol-2-yl)ethyl)piperidine-2,6-dione |
| 100 | N-(2-(3-methoxyisoxazol-5-yl)ethyl)piperidine-2,6-dione |
| 101 | N-(3-(thiophen-2-yl)propyl)piperidine-2,6-dione |
| 102 | N-(3-(pyridin-2-yl)propyl)piperidine-2,6-dione |
| 103 | N-(2-(6-chloropyridin-3-yl)ethyl)piperidine-2,6-dione |
| 104 | N-(2-(3-chloroisoxazol-5-yl)ethyl)piperidine-2,6-dione |
| 105 | N-(3-(3-methoxyisoxazol-5-yl)propyl)piperidine-2,6-dione |
| 106 | N-(3-(3-chloroisoxazol-5-yl)propyl)piperidine-2,6-dione |
| 107 | N-(2-(1H-indol-2-yl)ethyl)piperidine-2,6-dione |
| 108 | N-(3-(pyridin-4-yl)propyl)piperidine-2,6-dione |
| 109 | N-(2-(6-methoxypyridin-3-yl)ethyl)piperidine-2,6-dione |
| 110 | N-(2-(thiazol-4-yl)ethyl)piperidine-2,6-dione |
| 111 | N-(2-(oxazol-5-yl)ethyl)piperidine-2,6-dione |
| 112 | N-(2-(1H-pyrazol-4-yl)ethyl)piperidine-2,6-dione |

TABLE 1-continued

| Number of a compound | Structure |
|---|---|
| 113 | (structure) |
| 114 | (structure) |
| 115 | (structure) |

The pharmaceutically acceptable salts of the compounds according to the present invention can be selected from additive salts of organic acids (for example, formiate, acetate, maleate, tartrate, methanesulfonate, benzenesulfonate, toluenesulfonate, etc.), additive salts of inorganic acids (for example, hydrochloride, hydrobromide, sulphate, phosphate, etc.), and salts with amino acids (for example, an aspartic acid salt, a glutamic acid salt, etc.), preferably chlorohydrates and acetates.

The most preferred known compounds that can be used in the pharmaceutical composition and methods for the treatment according to the present invention are glutarimide derivatives represented in Table 2.

TABLE 2

| The number of a compound | Structure |
|---|---|
| 116 | (structure) |
| 117 | (structure) |

TABLE 2-continued

| The number of a compound | Structure |
|---|---|
| 118 | (structure) |
| 119 | (structure) |
| 120 | (structure) |
| 121 | (structure) |
| 122 | (structure) |
| 123 | (structure) |
| 124 | (structure) |
| 125 | (structure) |

TABLE 2-continued

| The number of a compound | Structure |
|---|---|
| 126 | [structure: glutarimide N-substituted with CH(COOH)-CH2-indole] |
| 127 | [structure: glutarimide N-substituted with -CH2CH2-thiophene] |
| 128 | [structure: glutarimide N-substituted with -CH2CH2-furan] |
| 129 | [structure: glutarimide N-substituted with -CH2CH2CH2-furan] |
| 130 | [structure: glutarimide N-substituted with -CH2CH2-pyrrole] |
| 131 | [structure: glutarimide N-substituted with -CH2CH2-triazole] |
| 132 | [structure: glutarimide N-substituted with -CH2CH2-furan (3-position)] |

Compounds according to the present invention can be prepared by a method comprising heating of initial dicarboxylic acid monoamides of general formula II with a dehydrating agent in an organic solvent or in the dehydrating agent, optionally with sodium acetate.

Compounds of general formula II and methods for preparing thereof are disclosed in the publication of international application WO 1999/001103.

The step of heating is preferably performed at temperature of 90 to 120° C., more preferably at 100° C., and more preferably under boiling.

The dehydrating agent used in the method may be selected from dixarboxylic acid anhydrides, organic acid chloroanhydrides, and carbonyldiimidazole.

A preferred dehydrating agent used in the method is glutaric anhydride, propionic anhydride, acetic anhydride, acetic acid chloroanhydride, or carbonyldiimidazole. The most preferred variant is propionic anhydride in toluene, glutaric anhydride preferably in dimethylformamide, acetic anhydride in dioxane, or acetic acid chloroanhydride in acetic acid.

The most preferred variant of the method is a method, wherein a dehydrating agent and a solvent are acetic acid and heating is performed at 90-100° C.

If a compound comprises additional functional groups (for example, OH, $NH_2$, COOH), they must be previously protected with conventional protective groups commonly used in the organic synthesis, such as benzyloxycarbonyl, benzyl, and acetyl groups. Upon completion of the synthesis, these groups are optionally removed, for example, by hydrogenation.

The claimed methods for preparing N-substituted glutarimides of general formula I substituted on the nitrogen atom are simple in implementation, conducted under quite mild conditions, are free of by-products, readily reproducible, and provide target products with a high yield (up to 82%) and of a high purity.

Glutarimide derivatives of general formula I are therapeutically active against upper respiratory tract diseases.

In particular, compounds according to the present invention are useful in the treatment of the upper respiratory tract diseases of bacterial, viral, or viral and bacterial etiology, or caused by other factors. In particular, such diseases are rhinosinusitis, diseases caused by RNA-comprising viruses, such as rhinovirus, Coxsackie virus, respiratory syncytial virus and influenza virus, for example, exacerbations of asthma, chronic obstructive pulmonary disease, bronchitis and mucoviscidosis, which are caused by rhinovirus, influenza virus and/or respiratory syncytial virus.

The compounds according to the present invention are administered in an effective amount that provides a desired therapeutic effect.

The compounds of general formula (I) may be administered orally, topically, parenterally, intranasally, by inhalation, and rectally in a unit dosage form comprising non-toxic pharmaceutically acceptable carriers. The term "oral administration" as used in the present invention means subcutaneous, intravenous, intramuscular or intrathoric injection or infusion.

The compounds according to the present invention can be administered to a patient at a dose of from 0.1 to 100 mg/kg of the body weight once daily, preferably at a dose of from 0.25 to 25 mg/kg one or more times a day.

In addition, it should be noted that a particular dose for a particular patient depends on many factors, including the activity of a certain compound, patient's age, body weight, gender, general health condition and diet, the time and route of administration of a pharmaceutical agent and the rate of its excretion from the body, a specific combination of drugs, and the severity of a disease in an individual to be treated.

The pharmaceutical compositions according to the present invention comprise a compound of general formula (I) in an amount effective to achieve a desired technical result, and can be administered in a unite dosage form (for example, in a solid, semi-solid, or liquid form) comprising the compounds according to the present invention as an active agent in a mixture with a carrier or an excipient suitable for intramuscular, intravenous, oral and sublingual administration, administration by inhalation, intranasal and intrarectal administration. The active ingredient can be in a composition together with conventional nontoxic pharmaceutically acceptable carriers suitable for the manufacture of solutions, tablets, pills, capsules, coated pills, emulsions, suspensions, ointments, gels, and any other dosage forms.

As an excipient, various compounds can be used, such as saccharides, for example, glucose, lactose, of sucrose; mannitol or sorbitol; cellulose derivatives; and/or calcium phosphates, for example, tricalcium phosphate or calcium hydrophosphate. As a binder, the following compounds can be used, such as a starch paste (for example, corn, wheat, rice, or potato starch), gelatin, tragacanth, methylcellulose, hydroxypropylmethylcellulose, sodium carboxymethylcellulose, and/or polyvinylpyrrolidone. Optionally used disintegrants are the above-mentioned starches and carboxymethylstarch, crosslinked polyvinylpyrrolidone, agar-agar, or alginic acid or a salt thereof, such as sodium alginate.

Additives that can be optionally used are flowability-control agents and lubricants, such as silicon dioxide, talc, stearic acid and salts thereof, such as magnesium stearate or calcium stearate, and/or propylene glycol.

The core of a coted pill is usually coated with a layer that is resistant to the action of gastric acid. For this purpose a concentrated solution of saccharides can be used, wherein said solutions can optionally comprise gum arabic, talc, polyvinylpyrrolidone, polyethylene glycol, and/or titanium dioxide, and suitable organic solvents or a mixture thereof.

Stabilizers, thickening agents, colorants, and fragrances also can be used as additives.

As an ointment base, there are usable hydrocarbon ointment bases, such as white Vaseline and yellow Vaseline (*Vaselinum album* and *Vaselinum flavum*, respectively), Vaseline oil (*Oleum Vaselini*), and white ointment and liquid ointment (*Unguentum album* and *Unguentum flavum*, respectively), wherein solid paraffin or wax can be used as an additive providing a firmer texture; absorptive ointment bases, such as hydrophilic Vaseline (*Vaselinum hydrophylicum*), lanoline (*Lanolinum*), and cold cream (*Unguentum leniens*); water-removable ointment bases, such as hydrophilic ointment (*Unguentum hydrophylum*); water-soluble ointment bases, such as polyethylene glycol ointment (*Unguentum Glycolis* Polyaethyleni); bentonite bases; and others.

A base for gels may be selected from methylcellulose, sodium caboxymethylcellulose, oxypropylcellulose, polyethylene glycol or polyethylene oxide, and carbopol.

In preparing a unit dosage form, the amount of an active agent used in combination with a carrier can vary depending on a recipient to be treated and on a particular route of administration of a therapeutic agent.

For example, when the compounds according to the present invention are used in the form of a solution for injection, the amount of the active agent in this solution is 0.01-5 wt. %. A diluent may be selected from a 0.9% sodium chloride solution, distilled water, a Novocain solution for injection, Ringer's solution, a glucose solution, and specific solubilizing adjuvants. When the compounds according to the present invention are administered in tablet or suppository form, their amount is up to 200 mg per unit dosage form.

Dosage forms according to the present invention are prepared by conventional procedures, such as blending, granulation, forming coating pills, dissolution, and lyophilization.

It should be noted that the compounds according to the present invention are biologically active in doses by two-three orders of magnitude lower than the doses of comparative known medicaments and have almost the same efficiency. In addition, there are no registered adverse effects caused by these compounds and they do not have contraindications for administration as well. Furthermore, the toxicity tests of the compounds according to the present invention showed no registered fatal cases among experimental animals at an oral dose of 3000 mg/kg.

The detailed description of the compounds according to the present invention, their preparation and studies of their activity are disclosed in the following examples that are intended for purposes of illustration only and are not intended to limit the scope of the invention.

Examples of Synthesis of Glutarimide Derivatives of General Formula I

Materials and Methods

Identity of obtained compounds were assessed by the thin-layer chromatography (TLC) method on plates "Kieselgel 60 F254" ("Merck", German) in a solvent system: chloroform-methanol (8:2) (1); and chloroform-methanol (9:1) (2).

Chromatograms and electrophoregrams were stained with chloro-tetramethylbenzene reagent and Pauly's reagent.

Fourier-IR spectra were recorded on a "Magna 750" spectrometer with KBr tablets ("Nicolet" (US)).

Shimadzu Analytical HPLC SCL10Avp LC/MS system was used for the analysis of multicomponent mixtures on a mass spectrometer PE SCIEX API 165 (150) (Canada).

Analytical-scale reversed phase HPLC was performed on a Shimadzu HPLC chromatograph under the following conditions: column: Symmetry C18, 250×4.6 mm; elution gradient system: water with 0.1% HCOOH:acetonitrile with 0.1% HCOOH (condition A); column: Merk.LiChroCART 250×4 mm 5 µm. LiChrospher 100RP-8E 5 µm.C8, Serial number 1.50837.0001; elution gradient system: an ammonium acetate buffer solution (pH 7.5):acetonitrile (condition B); a buffer with 0.0025M sodium 1-hexylsulfonate (pH 3):acetonitrile (condition C); and column: Luna C18 (2) 100 A, 250×4.6 mm (Serial number 599779-23), elution gradient system: a phosphate buffer solution (pH 3.0):methanol (condition D).

$^1$H NMR spectra were registered on Bruker AMX-400 (German) spectrometers.

High-resolution mass-spectra were obtained on a time-of-flight-assisted mass-spectrometer by the method of matrix laser-desorption ionization with 2,5-dihydroxybensoic acid used as a matrix, on an Ultraflex mass spectrometer ("Bruker", German).

Example 1

Preparation of 1-(2-(1H-imidazol-4-yl)ethyl)piperidine-2,6-dione (compound 1)

2-(Imidazol-4-yl)-ethanamide of pentandioic-1,5 acid (1 g; 4.4 mmol) dissolved in 5 ml of acetic acid was filled in a flat-bottom flask. One and half equivalents of acetylchloride were added dropwise. The reaction mass was allowed to stand for 12 hours under stirring at 90° C. The reaction was controlled by $^1$H-NMR spectroscopy. The reaction mixture was cooled, and the solvent was removed under vacuum. The formed residue was dissolved in the minimum amount of water, and sodium carbonate was added batchwise under stirring to reach the pH value of 8-9. The precipitate was filtered and washed with a small amount of water, and dried. After filtration, the stock solution was extracted three rimes with methylene chloride. The combined stock solution was dried over sodium sulfate, and the solvent was removed under vacuum. The formed residue was dried, combined with the first portion (after filtration), and a the amount of the obtained 1-(2-(1H-imidazol-4-yl)ethyl)piperidine-2,6-dione in the form of a light powder was 0.52 g (yield, 56%). LC/MS, an individual peak at a retention time of 1.57 min, [M+H]$^+$=208, $^1$H-NMR (CD$_3$OD), δ, m.d.: 1.87-1.93 (m, 2H, 4'-CH$_2$), 2.61-2.65 (t, 4H, 3',5'-CH$_2$), 2.76-2.80 (t, 2H, 1-CH$_2$), 3.96-4.00 (t, 2H, 2-CH$_2$), 6.8 (s, 1H, 5"-CH-Im), 7.55 (s, 1H, 2"-CH-Im).

Example 2

Preparation of 1-(2-1H-imidazol-4-yl)ethyl)piperidine-2,6-dione (compound 1)

2-(Imidazol-4-yl)-ethanamide of pentandioic-1,5 acid (1 g; 4.4 mmol) and 10 ml of propionic anhydride were filled in a flat-bottom flask. Three equivalents of sodium acetate were added, and the mixture was allowed to stand under stirring at 120° C. for 12 hours. The reaction was controlled by $^1$H-NMR spectroscopy. The reaction mixture was diluted with a three-fold excess of water under cooling and stirring, and sodium carbonate was added batchwise to reach the pH value of 8-9. The reaction mixture was extracted with ethyl acetate three times. A combined organic stock solution was dried over sodium sulfate, and the solvent was removed. The amount of the obtained 1-(2-(1H-imidazol-4-yl)ethyl)piperidine-2,6-ione in the form of light yellow crystals was 0.37 g (yield, 40%). [M]$^+$207.9. $^1$H-NMR (CD$_3$OD), δ, m.d.: 1.85-1.91 (m, 2H, 4'-CH$_2$), 2.60-2.63 (t, 4H, 3',5'-CH$_2$), 2.73-2.77 (t, 2H, 1-CH$_2$), 3.95-4.00 (t, 2H, 2-CH$_2$), 6.8 (s, 1H, 5"-CH-Im), 7.52 (s, 1H, 2"-CH-Im).

Example 3

Preparation of 1-(2-(1H-imidazol-4-yl)ethyl)piperidine-2,6-dione (compound 1)

2-(Imidazol-4-yl)-ethanamide of pentandioic-1,5 acid (100 g, 0.44 mol), 80 ml (0,85 mol) acetic anhydride (80 ml, 0.85 mol) and toluene (200 ml) were added to 1 L cone flask equipped with a reflux condenser. The obtained suspension was heated until the solid was dissolved, and the solution was refluxed for 6 to 8 hours. The solvent was removed under vacuum, and 300 ml of methanol were added to the resulting oil, and the solvent was repeatedly removed under vacuum. The residue was dissolved in 300 ml of methylene chloride and 65 ml of triethylamine were added thereto. The resulting solution was concentrated under vacuum and allowed to stand for 18 hours at +4° C. The residue was filtered through a Buchner funnel (d=10 cm), washed three times with isopropanol, and dried at +70° C. The degree of purity was controlled by a TLC method (Rf$_{product}$, 0.54; (1)). In case of a need for additional purification and clarification, the product was recrystallized, and a hot solution of the product was simultaneously treated with carbon black/carbon. The amount of the obtained 1-(2-(1H-imidazol-4-yl) ethyl)piperidine-2,6-dione was 73.6 g (yield, 80%). [M+H]$^+$ 208, $^1$H-NMR (CD$_3$OD), δ, m.d.: 1.87-1.93 (m, 2H, 4'-CH$_2$), 2.61-2.65 (t, 4H, 3',5'-CH$_2$), 2.76-2.80 (t, 2H, 1-CH$_2$), 3.96-4.00 (t, 2H, 2-CH$_2$), 6.8 (s, 1H, 5"-CH-Im), 7.55 (s, 1H, 2"-CH-Im).

The following compounds were prepared by the above-disclosed method:

| Number of a compound | Structural formula | Physical and chemical data |
|---|---|---|
| 4 | (piperidine-2,6-dione with ethyl-pyrrolidine substituent) | LC/MS: an individual peak at a retention time of 1.0 min, [M + H]$^+$ = 211. HPLC under condition A: an individual peak at a retention time of 10.9 min |
| 11 | (piperidine-2,6-dione with ethyl-(N-methylpyrrole) substituent) | LC/MS: an individual peak at a retention time of 1.08 min, [M + H]$^+$ = 220. HPLC under condition A: an individual peak at a retention time of 17.5 min |

Example 4

Preparation of 1-(2-(1H-imidazol-4-yl)ethyl)piperidine-2,6-dione (compound 1)

Glutaric anhydride (3.5 g, 0.031 mol) was added to 2-(imidazol-4-yl)-ethanamide of pentandioic-1,5 acid (4.5 g; 0.020 mol) dissolved under heating in 25 ml of N,N'-formamide, and the reaction mixture was heated to 100° C. for 4-6 hours. The completeness of the reaction was checked by a TLC or electrophoresis method. The solvent was removed under vacuum, the oil-like residue was dissolved in 50 ml of water, and the solution was passed through a column filled with 70 ml of Amberlite IRA-96. The eluate comprising the target compound was collected, and the solvent was removed under vacuum. The resulting solid residue was recrystallized from chloroform. The amount of the obtained 1-(2-(1H-imidazol-4-yl)ethyl)piperidine-2,6-dione was 3.1 g (75.6%).

Rf 0.43 (2). [M]$^+$207.9.

$^1$H-NMR (CD$_3$OD), δ, m.d.: 1.87-1.93 (m, 2H, 4'-CH$_2$), 2.61-2.65 (t, 4H, 3',5'-CH$_2$), 2.76-2.80 (t, 2H, 1-CH$_2$), 3.96-4.00 (t, 2H, 2-CH$_2$), 6.8 (s, 1H, 5"-CH-Im), 7.55 (s, 1H, 2"-CH-Im).

HPLC under condition A: an individual peak at a retention time of 15.5 min.

Fourier-IR spectrum (in a KBr table, ν, cm$^{-1}$): 3136, 3070, 2833 (—NH-val.), 1720, 1670 (CO, cycl. imide), 1339, 1257 (—CH$_2$—). Found, %: S, 57.60; H, 6.12; N, 21.17. C$_{10}$H$_{13}$N$_3$O$_2$. Calculated, %: S, 57.96; H, 6.32; N, 20.28.

Example 5

Preparation of 1-(2-(1H-imidazol-4-yl)ethyl)piperidine-2,6-dione (compound 1)

2-(Imidazol-4-yl)-ethanamide of pentandioic-1,5 acid (100 g, 0.44 mol), propionic anhydride (102 ml, 0.80 mol) and toluene (200 ml) were added to 1 L cone flask equipped with a reflux condenser. The obtained suspension was heated until the solid is dissolved, and the solution was refluxed for 8 to 9 hours. The solvent was removed under vacuum, and 300 ml of methanol were added to the resulting oil, and the solvent was repeatedly removed under vacuum. The residue was dissolved in 300 ml of methylene chloride and 65 ml of triethylamine were added thereto. The resulting solution was concentrated under vacuum to evaporate of about 70% of methylene chloride and then was allowed to stand for 18 hours at 0 to +4° C. The residue was filtered, washed three times with isopropanol cooled to from 0 to −5° C. The crude product was recrystallized, and a hot solution of the product was simultaneously treated with carbon black/carbon. The degree of purity was controlled by a TLC method (Rf$_{product}$ 0.54; (1)). The solution of the product was subjected to a hot filtration on a "MILLIPORE" filtration system (0.45 μm), and dried under vacuum in a drying oven at +70° C. The amount of the obtained 1-(2-(1H-imidazol-4-yl)ethyl)piperidine-2,6-dione was 60.0 g, yield—65%. $^1$H-NMR (400.13 MHz, DMSO-d$_6$, δ, m.d., J/Hz): 1.81 (m, 2H, CH$_2$CH$_2$CH$_2$); 2.58 (m, 6H, CH$_2$C, CH$_2$CH$_2$CH$_2$); 3.83 (t, 2H, CH$_2$N, J=7.8 Hz); 6.77 (bs, 1H, CCH) 7.48 (bs, 1H, NCHN); 11.8 (bs, 1H, NH).

Example 6

Preparation of 1-(2-(1H-imidazol-4-yl)ethyl)piperidine-2-dione (compound 1)

N$^\beta$-Glutarylhistamine (5.0 g; 0.022 mol) was heated in 12 ml of acetic anhydride to 100° C. for 4-6 hours. The completeness of the reaction was checked by a TLC or electrophoresis method. The solvent was removed from the reaction mixture under vacuum, and the resulting solid residue was recrystallized from isopropanol alcohol. The amount of the obtained 1-(2-(1H-imidazol-4-yl)ethyl)piperidine-2,6-dione was 3.7 g (80%). Rf 0.43 (2). Found %: C, 57.73; H, 6.15; N, 20.17. C$_{10}$H$_{13}$N$_3$O$_2$. Calculated %: S, 57.96; H, 6.32; N, 20.28.

Example 7

1-[2-(1H-benzothiazol-2-yl)ethyl]piperidine-2-dione (compound 7)

A mixture of 5-{[2-(1,3-benzothiazol-2-yl)ethyl]amino}-5-oxopentanoic acid (22 g; 0.075 mol) and acetic anhydride (23 g; 0.225 mol) were boiled in 150 ml of dioxane for 3 hours. Dioxane was removed under vacuum, 200 ml of water was added and the mixture was neutralized with 30% sodium hydroxide to neutral pH. The precipitated oil was triturated in crystals. The residue was purified by chromatography (SiCO$_2$ 60-100 μm, eluent: ethylacetate-hexane (1:1)). The amount of the obtained 1-[2-(1H-imidazol-2-yl)ethyl]piperidine-2,6-dione was 16.5 g (79.9%). LC/MS: an individual peak at a retention time of 2.26 min, [M+H]$^+$275. HPLC under condition A: an individual peak at a retention time of 9.34 min. $^1$H-NMR (400.13 MHz, DMSO-d$_6$, δ, m.d., J/Hz): 1.85 (quint, 2H, CH$_2$CH$_2$CH$_2$, J=6.8 Hz); 2.59 (t, 4H, CH$_2$CH$_2$CH$_2$, J=6.8 Hz); 3.24 (t, 2H, CH$_2$S, J=7.3 Hz); 4.08 (t, 2H, CH$_2$N, J=7.3 Hz); 7.43, 7.49 (t, 1H, Ar, J=7.6 Hz); 7.96, 8.04 (d, 1H, Ar, J=7.6 Hz).

The following compounds were prepared by the above-disclosed method:

| Number of a compound | Structural formula | Physical and chemical data |
| --- | --- | --- |
| 6 | (piperidine-2,6-dione linked via ethyl to thiazole) | LC/MS: an individual peak at a retention time of 1.43 min, [M + H]$^+$ = 225. HPLC under condition D: an individual peak at a retention time of 31.28 min. $^1$H-NMR (400.13 MHz, DMSO-d$_6$, δ, m.d., J/Hz): 1.82 (quint, 2H, CH$_2$CH$_2$CH$_2$, J = 6.5 Hz); 2.58 (t, 4H, CH$_2$CH$_2$CH$_2$, J = 6.5 Hz); 3.12 (t, 2H, CH$_2$C, J = 7.4 Hz); 3.97 (t, 2H, CH$_2$N, J = 7.4 Hz); 7.58 (d, 1H, SCH, J = 3.2 Hz); 7.70 (d, 1H, NCH, J = 3.2 Hz) |
| 8 | (piperidine-2,6-dione linked via ethyl to imidazole) | LC/MS: an individual peak at a retention time of 0.41 min, [M + H]$^+$ = 208. HPLC under condition B: an individual peak at a retention time of 16.72 min. $^1$H-NMR (400.13 MHz, DMSO-d$_6$, δ, m.d., J/Hz): 1.82 (quint, 2H, CH$_2$CH$_2$CH$_2$) J = 6.5 Hz); 2.57 (t, 4H, CH$_2$CH$_2$CH$_2$, J = 6.5 Hz); 2.72 (t, 2H, CH$_2$C, J = 7.5 Hz); 3.90 (t, 2H, CH$_2$N, J = 7.5 Hz); 6.86 (s, 2H, CHN); 11.72 (bs, 1H, NH) |

Example 8

1-[2-(1H-pyridyl-3-yl)ethyl]piperidine-2,6-dione (compound 10)

2-(pyridyl-3-yl)-ethanamide of pentandioic-1,5 acid (29.00 g; 0.12 mol) and anhydrous sodium acetate (5.9 g; 0.07 mol) were dissolved in 200 ml of acetic anhydride. The reaction mixture was heated to simmering and was further refluxed for 18 hours. After completion of the reaction, the solvent was removed under vacuum, and a residue was dissolved in 500 ml of dichloromethane, washed two times with 100 ml portions of a 3% soda solution and dried over sodium sulfate. The solvent was removed under vacuum, and the resulting oil was dissolved in dioxane. A 3M HCl solution in dioxane was added, and the precipitate was filtered and recrystallized from 125 g of isopropanol. The product in the form of hydrochloride was obtained in an amount of 25 g (yield, 80%). LC/MS: an individual peak at a retention time of 0.5 min, [M+H]$^+$218. HPLC under condition D: an individual peak at a retention time of 16.72 min. $^1$H-NMR (400.13 MHz, DMSO-d$_6$, δ, m.d., J/Hz): 1.78 (quint, 2H, CH$_2$CH$_2$CH$_2$, J=6.4 Hz); 2.56 (t, 4H, CH$_2$CH$_2$CH$_2$, J=6.4 Hz); 2.73 (t, 2H, CH$_2$C, J=7.3 Hz); 3.86 (t, 2H, CH$_2$N, J=7.3 Hz); 7.30 (dd, 1H, 5-Pyr, J=7.8, 4.5 Hz); 7.60 (d, 1H, 4-Pyr, J=7.8 Hz); 8.37 (d, 1H, 2-Pyr, J=1.5 Hz); 8.41 (dd, 1H, 6-Pyr, J=4.5, 1.5 Hz).

The following compounds were prepared by the above-disclosed method:

| Number of a compound | Structural formula | Physical and chemical data |
|---|---|---|
| 2 | [structure: 4-methylpiperidine-2,6-dione with N-CH$_2$CH$_2$-imidazole] | LC/MS: an individual peak at a retention time of 0.5 min, [M + H]$^+$ = 222. HPLC under condition D: an individual peak at a retention time of 19.7 min. $^1$H-NMR (400.13 MHz, DMSO-d$_6$, δ, m.d., J/Hz): 1.82 (quint, 2H, CH$_2$CH$_2$CH$_2$, J = 6.5 Hz); 2.58 (t, 4H, CH$_2$CH$_2$CH$_2$, J = 6.5 Hz); 3.12 (t, 2H, CH$_2$C, J = 7.4 Hz); 3.97 (t, 2H, CH$_2$N, J = 7.4 Hz); 7.58 (d, 1H, SCH, J = 3.2 Hz); |
| 3 | [structure: 4,4-dimethylpiperidine-2,6-dione with N-CH$_2$CH$_2$-imidazole] | LC/MS: an individual peak at a retention time of 0.41 min, [M + H]$^+$ = 236. HPLC under condition D: an individual peak at a retention time of 22.16 min. $^1$H-NMR (400.13 MHz, DMSO-d$_6$, δ, m.d., J/Hz): 0.91 (s, 6H, CH$_3$); 2.58 (m, 6H, CH$_2$C, CH$_2$CCH$_2$); 3.86 (t, 2H, CH$_2$N, J = 7.3 Hz); 6.60, 6.85 (bs, 1H, CCH); 7.50 (bs, 1H, NCHN); 11.8 (bs, 1H, NH) |
| 5 | [structure: piperidine-2,6-dione with N-CH$_2$CH$_2$-(N-methyl)imidazole] | LC/MS: an individual peak at a retention time of 0.21 min, [M + H]$^+$ = 222. HPLC under condition B: an individual peak at a retention time of 20.7 min. $^1$H-NMR (400.13 MHz, DMSO-d$_6$, δ, m.d., J/Hz): 1.82 (quint, 2H, CH$_2$CH$_2$CH$_2$, J = 6.4 Hz); 2.53 (m, 2H, CH$_2$C); 2.58 (t, 4H, CH$_2$CH$_2$CH$_2$, J = 6.4 Hz); 3.57 (s, 3H, NMe); 3.80 (t, 2H, CH$_2$N, J = 7.8 Hz); 6.85 (s, 1H, CCH); 7.42 (s, 1H, NCHN) |

Example 9

1-(2-(1H-imidazol-4-yl)ethyl)piperidine-2,6-dione (compound 1)

N,N'-dimethylformamide (60 ml) and 2-(imidazol-4-yl)-ethanamide of pentandioic-1,5 acid (20 g) were filled in a flat-bottom flask (250 ml). Carbonyldiimidazole (17.3 g; 1.2 equiv.) was added under vigorous stirring. The reaction mixture was heated to 90° C. for 2 hours. The reaction was controlled by $^1$H-NMR spectroscopy (a sample (0.5 ml) was diluted with a sulphuric ether, and the precipitate was dissolved in DMSO-$d_6$). When the initial 2-(imidazol-4-yl)-ethanamide of pentandioic-1,5 acid was absent in the reaction mass, the mass was cooled and poured out into a three-fold volume of methyl tert-butyl ether (180 ml). The reaction mixture was allowed to stand for 1 hour, and the precipitate was filtered, washed with 60 ml of methyl tert-butyl ether, and dried. The yield of the crude 1-(2-(1H-imidazol-4-yl)ethyl)piperidine-2,6-dione was 12.4 g (67%).

The crude 1-(2-(1H-imidazol-4-yl)ethyl)piperidine-2,6-dione (12 g) and isopropanol (36 mg) were filled in a 100 ml flat-bottom flask. The mixture was heated to complete dissolution of the residue, then 1.2 g of activated carbon were added, and the mixture was allowed to stand for an hour. The solution being hot was filtered through a preheated ceramic filter. The residue on the filter was washed with 6 ml of hot isopropanol. The hot stock solution was cooled to room temperature and allowed to stand for a night under stirring for crystallization. Precipitated crystals were filtered, washed with 6 ml of cool isopropanol, and dried. After recrystallization, the amount of the obtained 1-(2-(1H-imidazol-4-yl)ethyl)piperidine-2,6-dione was 10.1 g (84%). The product was analyzed with an LC/MS method: an individual peak at a retention time of 1.57 min; [M+H]$^+$208.

$^1$H-NMR (CD$_3$OD), δ, m.d.: 1.87-1.93 (m, 2H, 4'-CH$_2$); 2.61-2.65 (t, 4H, 3',5'-CH$_2$); 2.76-2.80 (t, 2H, 1-CH$_2$); 3.96-4.00 (t, 2H, 2-CH$_2$); 6.8 (c, 1H, 5"-CH-Im); 7.55 (c, 1H, 2"-CH-Im).

Compounds 9, 12-115 represented in Table 3 were synthesized by analogous methods.

TABLE 3

| Number of a compound | Structural formula | Constants |
|---|---|---|
| 9 | | LC/MS: an individual peak at a retention time of 0.21 min, [M + H]$^+$ = 219. $^1$H-NMR (400.13 MHz, DMSO-d$_6$, δ, m.d., J/Hz): 1.82 (quint, 2H, CH$_2$CH$_2$CH$_2$, J = 6.4 Hz); 2.58 (t, 4H, CH$_2$CH$_2$CH$_2$, J = 6.4 Hz); 3.08 (t, 2H, CH$_2$C, J = 7.3 Hz); 3.96 (t, 2H, CH$_2$N, J = 7.3 Hz); 7.90 (d, 2H, 3,5-Pyr, J = 7.8 Hz); 8.80 (d, 2H, 2,6-Pyr, J = 7.8 Hz) |
| 12 | | LC/MS: an individual peak at a retention time of 0.21 min, [M + H]$^+$ = 224. $^1$H-NMR (400.13 MHz, DMSO-d$_6$, δ, m.d., J/Hz): 1.79 (quint, 2H, COCH$_2$CH$_2$CH$_2$CO, J = 6.6 Hz), 2.58 (t, 4H, COCH$_2$CH$_2$CH$_2$CO, J = 6.6 Hz), 2.72 (t, 2H, CH$_2$C, J = 7.8 Hz), 3.84 (t, 2H, CH$_2$N, J = 7.8 Hz), 6.97 (d, 1H, 4-thiophene, J = 4.6 Hz), 7.20 (d, 1H, 2-thiophene, J = 3.1 Hz), 7.45 (dd, 1H, 5-thiophene, J = 4.6, 3.1 Hz) |
| 13 | | LC/MS: an individual peak at a retention time of 0.21 min, [M + H]$^+$ = 219. $^1$H-NMR (400.13 MHz, DMSO-d$_6$, δ, m.d., J/Hz): 1.80 (quint, 2H, CH$_2$CH$_2$CH$_2$, J = 6.4 Hz); 2.55 (t, 4H, CH$_2$CH$_2$CH$_2$, J = 6.4 Hz); 3.20 (t, 2H, CH$_2$C, J = 7.3 Hz); 4.0 (t, 2H, CH$_2$N, J = 7.3 Hz); 7.82 (t, 1H, 4-Pyr, J = 4.5 Hz); 7.85 (d, 1H, 3-Pyr, J = 7.8 Hz); 8.41 (t, 1H, 5-Pyr, J = 1.5 Hz); 8.67 (d, 1H, 6-Pyr, J = 4.5 Hz). |
| 14 | | LC/MS: an individual peak at a retention time of 0.21 min, [M + H]$^+$ = 225. $^1$H-NMR (400.13 MHz, DMSO-d$_6$, δ, m.d., J/Hz): 1.3-1.4 (m, 6H, morph), 1.75 (quint, 2H, COCH$_2$CH$_2$CH$_2$CO, J = 6.6 Hz), 2.25 (m, 2H, CH$_2$N-morph), 2.3 (m, 4H, morph), 2.6 (t, 4H, COCH$_2$CH$_2$CH$_2$CO, J = 6.6 Hz), 3.7 (m, 3H, CH$_2$N) |

TABLE 3-continued

| Number of a compound | Structural formula | Constants |
|---|---|---|
| 15 | | [M + H]⁺ = 273. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 2.82 (t, 2H, CCH₂CH₂N, J = 8.8 Hz); 3.89 (t, 2H, CCH₂CH₂N, J = 8.8 Hz); 6.63 (d, 1H, Indole-6, J = 8.6 Hz); 6.75 (s, 1H, Indole-4); 7.16 (s, 1H, Indole-2); 7.43 (d, 1H, Indole-7, J = 8.6 Hz); 8.68 (bs, 1H, OH); 10.74 (s, 1H, NH) |
| 16 | | [M + H]⁺ = 210. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 2.73 (t, 2H, CCH₂CH₂N, J = 7.2 Hz); 3.34 (bs, 4H, NCH₂CH₂NH); 3.99 (t, 2H, CCH₂CH₂N, J = 7.2 Hz); 5.70 (bs, 1H, NH) |
| 17 | | [M + H]⁺ = 191. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 2.94 (t, 2H, CCH₂CH₂N, J = 7.2 Hz); 3.93 (t, 2H, CCH₂CH₂N, J = 7.2 Hz); 6.91 (s, 1H, SCCH); 8.11 (s, 1H, SNCH) |
| 18 | | [M + H]⁺ = 209. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 2.94 (t, 2H, CCH₂CH₂N, J = 7.2 Hz); 3.93 (t, 2H, CCH₂CH₂N, J = 7.2 Hz); 7.76 (s, 1H, CNCH); 8.11 (s, 1H, CNHCH) |
| 19 | | [M + H]⁺ = 210. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 3.20 (t, 2H, CCH₂CH₂N, J = 7.0 Hz); 3.93 (t, 2H, CCH₂CH₂N, J = 7.0 Hz); 7.76 (s, 1H, CH) |
| 20 | | LC/MS: an individual peak at a retention time of 0.21 min, [M + H]⁺ = 236. ¹H-NMR (400.13 MHz, DMSO-d₆, δ, m.d., J/Hz): 1.14 (s, 6H, CH₃), 1.73 (t, 2H, CH₂Me, J = 6.7 Hz), 2.59 (t, 2H, CH₂C, J = 7.5 Hz), 2.64 (t, 2H, CH₂CO, J = 6.7 Hz), 3.83 (t, 2H, CH₂N, J = 7.5 Hz), 6.75 (s, 1H, CCH), 7.48 (s, 1H, NHN), 11.79 (s, 1H, COOH). |

TABLE 3-continued

| Number of a compound | Structural formula | Constants |
|---|---|---|
| 21 | (2,6-dioxopiperidinyl)-CH(CH₂-indol-3-yl)-C(=O)-O-CH₃ | [M + H]⁺ = 315. ¹H-NMR (400.13 MHz, DMSO-d₆, δ, m.d., J/Hz): 1.84 (quint, 2H, CH₂CH₂CH₂, J = 7.5 Hz); 2.65 (t, 4H, CH₂CH₂CH₂, J = 7.5 Hz); 3.09 (d, 2H, CCH₂CHN, J = 11.7 Hz); 3.67 (s, 3H, CH₃); 4.16 (t, 1H, NCHCH₂, J = 11.7 Hz); 6.99 (dd, 1H, Indole-5, J = 7.4 Hz, J = 7.7 Hz); 7.04 (dd, 1H, Indole-6, J = 7.9 Hz, J = 7.4 Hz); 7.09 (s, 1H, Indole-2); 7.31 (d, 1H, Indole-7, J = 7.9 Hz); 7.52 (d, 1H, Indole-4, J = 7.7 Hz); 10.83 (s, 1H, NH) |
| 22 | (2,6-dioxopiperidinyl)-CH₂CH₂-(1-methylpyrrolidin-3-yl) | [M + H]⁺ = 225. ¹H-NMR (400.13 MHz, DMSO-d₆, δ, m.d., J/Hz): 1.77 (dt, 2H, CHCH₂CH₂NC, J = 8.5 Hz, J = 7.0 Hz); 1.84 (quint, 2H, CH₂CH₂CH₂, J = 7.5 Hz); 2.05 (dt, 2H, CH₂CH₂CH₂N, J = 6.0 Hz, J = 8.3 Hz); 2.13 (m, 1H, CH); 2.26 (s, 3H, CH₃); 2.68 (t, 4H, CH₂CH₂CH₂, J = 7.5 Hz); 3.01 (d, 2H, CHCH₂NCH₃, J = 7.2 Hz); 3.06 (t, 2H, CH₂CH₂NCH₃, J = 8.3 Hz); 3.68 (t, 2H, CHCH₂CH₂NC, J = 7.0 Hz) |
| 23 | (2,6-dioxopiperidinyl)-CH₂CH₂-pyrrolidinyl | LC/MS: an individual peak at a retention time of 0.21 min, [M + H]⁺ = 211. ¹H-NMR (300.13 MHz, DMSO-d₆, δ, m.d., J/Hz): 1.91 (m, 6H, COCH₂CH₂CH₂CO, NCH₂CH₂CH₂CH₂N), 2.65 (t, 4H, COCH₂CH₂CH₂CO, J = 6.5 Hz), 2.99 (s, 2H, NCH₂), 3.24 (d, 2H, NCH₂, J = 5.1 Hz), 3.53 (s, 2H, NCH₂), 3.96 (t, 2H, CONCH₂, J = 5.9 Hz), 10.80 (s, 1H, HCl), |
| 24 | (2,6-dioxopiperidinyl)-CH₂CH₂CH₂-imidazol-1-yl | LC/MS: an individual peak at a retention time of 0.21 min, [M + H]⁺ = 222. ¹H-NMR (300.13 MHz, DMSO-d₆, δ, m.d., J/Hz): 1.84 (m, 4H, COCH₂CH₂CH₂CO, NCH₂CH₂CH₂N), 2.57 (m, 4H, COCH₂CH₂CH₂CO), 3.64 (t, 2H, NCH₂, J = 7.0 Hz), 3.94 (t, 2H, NCH₂, J = 7.0 Hz), 6.87 (s, 1H, CHN=); 7.15 (s, 1H, CHN); 7.60 (s, 1H, NCHN) |
| 25 | (2,6-dioxopiperidinyl)-CH₂CH₂-(1-methylimidazol-5-yl) | [M + H]⁺ = 222. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 3.20 (t, 2H, CCH₂CH₂N, J = 7.0 Hz); 3.28 (s, 3H, CH₃); 3.93 (t, 2H, CCH₂CH₂N, J = 7.0 Hz); 6.70 (s, 1H, NCHC); 7.39 (s, 1H, NCHNCH₃) |
| 26 | (2,6-dioxopiperidinyl)-CH(CH₂-imidazol-4-yl)-C(=O)-O-CH₂CH₃ | [M + H]⁺ = 280. ¹H-NMR (400.13 MHz, DMSO-d₆, δ, m.d., J/Hz): 1.22 (t, 3H, CH₃, J = 7.1 Hz); 1.84 (quint, 2H, CH₂CH₂CH₂, J = 7.5 Hz); 2.56 (d, 2H, NHCCH₂CHC, J = 12.1 Hz); 2.65 (t, 4H, CH₂CH₂CH₂, J = 7.5 Hz); 4.12 (quint, 2H, COCH₂CH₃, J = 7.1 Hz); 4.16 (t, 1H, NCHCH₂C, J = 12.1 Hz); 6.79 (s, 1H, NCHC); 8.03 (s, 1H, NCHNH); 8.26 (bs, 1H, NH) |

TABLE 3-continued

| Number of a compound | Structural formula | Constants |
|---|---|---|
| 27 | | [M + H]$^+$ = 329. $^1$H-NMR (400.13 MHz, DMSO-d$_6$, δ, m.d., J/Hz): 1.22 (t, 3H, CH$_3$, J = 7.1 Hz); 1.84 (quint, 2H, CH$_2$CH$_2$CH$_2$, J = 7.5 Hz); 2.65 (t, 4H, CH$_2$CH$_2$CH$_2$, J = 7.5 Hz); 3.09 (d, 2H, CCH$_2$CHN, J = 11.7 Hz); 4.12 (quint, 2H, COCH$_2$CH$_3$, J = 7.1 Hz); 4.16 (t, 1H, NCHCH$_2$C, J = 11.7 Hz); 6.99 (dd, 1H, Indole-5, J = 7.4 Hz, J = 7.7 Hz); 7.04 (dd, 1H, Indole-6, J = 7.9 Hz, J = 7.4 Hz); 7.09 (s, 1H, Indole-2); 7.31 (d, 1H, Indole-7, J = 7.9 Hz); 7.52 (d, 1H, Indole-4, J = 7.7 Hz); 10.83 (s, 1H, NH) |
| 28 | | [M + H]$^+$ = 224. $^1$H-NMR (400.13 MHz, DMSO-d$_6$, δ, m.d., J/Hz): 2.54 (d, 4H, C(O)CH$_2$CHOH, J = 7.5 Hz); 3.20 (t, 2H, CCH$_2$CH$_2$N, J = 7.0 Hz); 3.93 (t, 3H, CCH$_2$CH$_2$N, J = 7.0 Hz); 3.94 (t, 1H, NCCH$_2$CHOH, J = 7.5 Hz); 5.24 (bs, 1H, OH); 6.86 (s, 1H, NCHC); 7.61 (s, 1H, NCHNH); 8.24 (bs, 1H, NH) |
| 29 | | [M + H]$^+$ = 224. $^1$H-NMR (400.13 MHz, DMSO-d$_6$, δ, m.d., J/Hz): 1.67 (dt, 2H, CH$_2$CHOH, J = 8.4 Hz, J = 12.5 Hz); 2.48 (t, 2H, CH$_2$CH$_2$CHOH, J = 12.5 Hz); 3.20 (t, 2H, CCH$_2$CH$_2$N, J = 7.0 Hz); 3.93 (t, 2H, CCH$_2$CH$_2$NC, J = 7.0 Hz); 4.60 (t, 1H, CHOH, J = 8.4 Hz); 5.38 (bs, 1H, OH); 6.86 (s, 1H, NCHC); 7.61 (s, 1H, NCHNH); 8.24 (s, 1H, NH) |
| 30 | | LC/MS: an individual peak at a retention time of 0.21 min, [M + H]$^+$ = 208. $^1$H-NMR (400.13 MHz, DMSO-d$_6$, δ, m.d., J/Hz): 1.78 (quint, 2H, COCH$_2$CH$_2$CH$_2$CO, J = 6.4 Hz), 2.55 (t, 4H, COCH$_2$CH$_2$CH$_2$CO, J = 6.5 Hz), 3.94 (t, 2H, CH$_2$N, J = 6.1 Hz), 4.05 (t, 2H, CH$_2$N, J = 6.1 Hz), 6.82 (s, 1H, CHN=); 7.09 (s, 1H, CHN); 7.54 (s, 1H, NCHN) |
| 31 | | [M + H]$^+$ = 284. $^1$H-NMR (400.13 MHz, DMSO-d$_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 3.20 (t, 2H, CCH$_2$CH$_2$N, J = 7.0 Hz); 3.93 (t, 2H, CCH$_2$CH$_2$N, J = 7.0 Hz); 7.23 (d, 1H, p-Ph, J = 7.4 Hz); 7.39 (dd, 2H, m-Ph, J = 7.6 Hz, J = 7.4 Hz); 7.70 (d, 2H, o-Ph, J = 7.6 Hz); 8.03 (s, 1H, NCHNH); 8.50 (s, 1H, NH) |

TABLE 3-continued

| Number of a compound | Structural formula | Constants |
|---|---|---|
| 32 | | [M + H]$^+$ = 222. $^1$H-NMR (400.13 MHz, DMSO-d$_6$, δ, m.d., J/Hz): 1.16 (d, 3H, CH$_3$, J = 7.0 Hz); 1.84 (quint, 2H, CH$_2$CH$_2$CH$_2$, J = 7.5 Hz); 2.63 (t, 4H, CH$_2$CH$_2$CH$_2$, J = 7.5 Hz); 3.14 (d, 2H, CCH$_2$CHCH$_3$, J = 9.5 Hz); 3.94 (quint, 1H, CH$_2$CNCHCH$_3$, J = 7.0 Hz, J = 9.5 Hz); 6.87 (s, 1H, NCHC); 7.81 (s, 1H, NCHNH); 8.24 (s, 1H, NH) |
| 33 | | [M + H]$^+$ = 222. $^1$H-NMR (400.13 MHz, DMSO-d$_6$, δ, m.d., J/Hz): 1.16 (d, 3H, CH$_3$, J = 7.0 Hz); 1.84 (quint, 2H, CH$_2$CH$_2$CH$_2$, J = 7.5 Hz); 2.63 (t, 4H, CH$_2$CH$_2$CH$_2$, J = 7.5 Hz); 3.14 (d, 2H, CCH$_2$CHN, J = 9.5 Hz); 3.94 (quint, 1H, CCH$_2$CHN, J = 7.0 Hz, J = 9.5 Hz); 6.87 (s, 1H, CCHN); 7.81 (s, 1H, NCHNH); 8.24 (s, 1H, NH) |
| 34 | | [M + H] = 209. $^1$H-NMR (400.13 MHz, DMSO-d$_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 3.20 (t, 2H, CCH$_2$CH$_2$N, J = 7.0 Hz); 3.93 (t, 2H, CCH$_2$CH$_2$N, J = 7.0 Hz); 7.95 (s, 1H, OCHC); 8.84 (s, 1H, OCHNC) |
| 35 | | LC/MS: an individual peak at a retention time of 0.21 min, [M + H]$^+$ = 209. $^1$H-NMR (400.13 MHz, DMSO-d$_6$, δ, m.d., J/Hz): 1.82 (quint, 2H, COCH$_2$CH$_2$CH$_2$CO, J = 6.5 Hz), 2.58 (t, 4H, COCH$_2$CH$_2$CH$_2$CO, J = 6.5 Hz), 2.79 (t, 2H, CH$_2$C, J = 7.6 Hz), 3.87 (t, 2H, CH$_2$N, J = 7.6 Hz), 7.59 (s, 1H, CHN=) |
| 36 | | LC/MS: an individual peak at a retention time of 0.21 min, [M + H]$^+$ = 210. $^1$H-NMR (400.13 MHz, DMSO-d$_6$, δ, m.d., J/Hz): 1.83 (quint, 2H, COCH$_2$CH$_2$CH$_2$CO, J = 6.5 Hz), 2.57 (t, 4H, COCH$_2$CH$_2$CH$_2$CO, J = 6.5 Hz), 3.04 (t, 2H, CH$_2$C, J = 7.2 Hz), 3.95 (t, 2H, CH$_2$N, J = 7.2 Hz), 16.09 (s, 1H, NH) |
| 37 | | [M + H]$^+$ = 242. $^1$H-NMR (400.13 MHz, DMSO-d$_6$, δ, m.d., J/Hz): 1.84 (quint, 2H, CH$_2$CH$_2$CH$_2$, J = 7.5 Hz); 2.51 (t, 2H, CCH$_2$CH$_2$N, J = 8.1 Hz); 2.68 (t, 4H, CCH$_2$CH$_2$CH$_2$, J = 7.5 Hz); 3.89 (t, 2H, CCH$_2$CH$_2$N, J = 8.1 Hz); 7.33 (d, 1H, CCHCHC, J = 8.3 Hz); 7.58 (s, 1H, NCCHC); 8.11 (d, 1H, SCCHCHC, J = 8.3 Hz) |

TABLE 3-continued

| Number of a compound | Structural formula | Constants |
|---|---|---|
| 38 | | [M + H]⁺ = 259. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 2.95 (t, 2H, CCH₂CH₂N, J = 8.1 Hz); 3.89 (t, 2H, CCH₂CH₂N, J = 8.1 Hz); 7.14 (d, 1H, CHCCH₂CH₂N, J = 7.5 Hz); 7.23 (dd, 1H, CHCHCH, J = 7.5 Hz, J = 8.2 Hz); 8.07 (d, 1H, NCCH, J = 8.2 Hz); 15.40 (bs, 1H, NH) |
| 39 | | [M + H]⁺ = 259. ¹H-NMR (400.13 MHz, DMSO-d₆, δ, m.d., J/Hz): 1.84 (quint, 2H, CH₂CH₂CH₂, J = 7.5 Hz); 2.51 (t, 2H, CCH₂CH₂N, J = 8.1 Hz); 2.68 (t, 4H, CCH₂CH₂CH₂, J = 7.5 Hz); 3.40 (s, 1H, NH); 3.89 (t, 2H, CCH₂CH₂N, J = 8.1 Hz); 7.33 (d, 1H, NHCCHCHC, J = 8.1 Hz); 7.58 (s, 1H, NCCHC); 8.31 (d, 1H, NHCCHCHC, J = 8.1 Hz) |
| 40 | | [M + H]⁺ = 243. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 3.20 (t, 2H, CCH₂CH₂N, J = 7.0 Hz); 3.93 (t, 2H, CCH₂CH₂N, J = 7.0 Hz); 8.43 (s, 1H, NCHN); 9.31 (s, 1H, SCHN) |
| 41 | | [M + H]⁺ = 258. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 2.95 (t, 2H, CCH₂CH₂N, J = 8.1 Hz); 3.89 (t, 2H, CCH₂CH₂N, J = 8.1 Hz); 6.88 (t, 1H, NNCHCHCH, J = 6.9 Hz); 7.43 (dd, 1H, NNCHCHCH, J = 6.8 Hz, J = 8.9 Hz); 7.63 (s, 1H, NCHC); 7.80 (d, 1H, NNCCH, J = 8.9 Hz); 8.71 (d, 1H, NNCHCHCH, J = 6.9 Hz) |
| 42 | | [M + H]⁺ = 258. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 2.82 (t, 2H, CCH₂CH₂NC, J = 8.8 Hz); 3.89 (t, 2H, CCH₂CH₂NC, J = 8.8 Hz); 7.15 (s, 1H, Indole-2); 7.61 (dd, 1H, Indole-5, J = 5.6 Hz, J = 8.1 Hz); 8.11 (d, 1H, Indole-4, J = 8.1 Hz); 8.45 (d, 1H, Indole-6, J = 5.6 Hz); 12.28 (s, 1H, NH) |
| 43 | | [M + H]⁺= 258. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 3.20 (t, 2H, CCH₂CH₂N, J = 7.0 Hz); 3.93 (t, 2H, CCH₂CH₂NC, J = 7.0 Hz); 6.87 (s, 1H, NCHC); 7.13 (dd, 1H, NCHCH, J = 7.0 Hz, J = 6.8 Hz); 7.46 (dd, 1H, NCCHCH, J = 6.8 Hz, J = 9.0 Hz); 7.66 (d, 1H, NCCHCH, J = 9.0 Hz); 8.57 (d, 1H, CH₂CNCHCH, J = 7.0 Hz) |

TABLE 3-continued

| Number of a compound | Structural formula | Constants |
|---|---|---|
| 44 | | [M + H]$^+$ = 252. $^1$H-NMR (400.13 MHz, DMSO-d$_6$, δ, m.d., J/Hz): 1.84 (quint, 2H, CH$_2$CH$_2$CH$_2$, J = 7.5 Hz); 2.65 (t, 4H, CH$_2$CH$_2$CH$_2$, J = 7.5 Hz); 3.09 (d, 2H, CCH$_2$CHCOOH, J = 11.7 Hz); 4.16 (t, 1H, NCHCH$_2$, J = 11.7 Hz); 6.35 (s, 1H, OCHCHC); 7.41 (s, 1H, OCHC); 7.53 (s, 1H, OCHCHC); 10.01 (s, 1H, OH) |
| 45 | | LC/MS: an individual peak at a retention time of 1.07 min, [M]$^+$ = 285. $^1$H-NMR (D$_6$-DMSO, 400 MHz) δ$_H$, 1.79-1.88 (m, 2H, CH$_2$CH$_2$CH$_2$), 2.57 (t, J = 6.4 Hz, 4H, CH$_2$CH$_2$CH$_2$), 2.90 (t, J = 8.0 Hz, 2H, CH$_2$CH$_2$N), 3.98 (t, J = 8.0 Hz, 2H, CH$_2$CH$_2$N), 7.46 (dd, J = 8.0, 4.8 Hz, 1H, CCHCHCHNCH), 8.27 (ddd, J = 8.0, 2.4, 1.6 Hz, 1H, CCHCHCHNCH) 8.58 (dd, J = 4.8, 1.6 Hz, 1H, CCHCHCHNCH), 9.13 (d, J = 2.4 Hz, 1H, CCHCHCHNCH), 13.88 (bs, 1H, NH(triazole)). |
| 46 | | LC/MS: an individual peak at a retention time of 0.97 min, [M + H]$^+$ = 265. $^1$H-NMR (D$_6$-DMSO, 400 MHz) δ$_H$, 1.77-1.84 (m, 2H, CH$_2$CH$_2$CH$_2$), 1.93 (s, CH$_3$), 2.54 (t, J = 6.4 Hz, 4H, CH$_2$CH$_2$CH$_2$), 3.97 (t, J = 6.4 Hz, 2H, NCH$_2$CH$_2$N), 4.04 (t, J = 6.4 Hz, 2H, NCH$_2$CH$_2$N), 6.37 (d, J = 1.6 Hz, 1H, CH(pyrazole)), 7.47 (d, J = 1.6 Hz, 1H, CH(pyrazole)), 10.20 (bs, 1H, NH) |
| 47 | | LC/MS: an individual peak at a retention time of 1.56 min, [M + H]$^+$ = 281. $^1$H-NMR (D$_6$-DMSO, 400 MHz) δ$_H$, 1.25 (s, 9H, C(CH$_3$)$_3$), 1.77-1.84 (m, 2H, CH$_2$CH$_2$CH$_2$), 2.56 (t, J = 6.4 Hz, 4H, CH$_2$CH$_2$CH$_2$), 3.06 (t, J = 7.2 Hz, 2H, CH$_2$CH$_2$CH$_2$), 3.95 (t, J = 7.2 Hz, 2H, CH$_2$CH$_2$N), 7.04 (s, 1H, CH(thiazole)). |
| 48 | | LC/MS: an individual peak at a retention time of 1.16 min, [M + H]$^+$ = 250. $^1$H-NMR (D$_6$-DMSO, 400 MHz) δ$_H$, 1.74-1.82 (m, 2H, CH$_2$CH$_2$CH$_2$), 2.03 (s, 3H, CCH$_3$), 2.11 (s, 3H, CCH$_3$), 2.38 (t, J = 8.0 Hz, 2H, CH$_2$CH$_2$N), 2.56 (t, J = 6.4 Hz, 4H, CH$_2$CH$_2$CH$_2$), 3.57 (s, 3H, NCH$_3$), 3.59 (t, J = 8.0 Hz, 2H, CH$_2$CH$_2$N). |
| 49 | | LC/MS: an individual peak at a retention time of 1.71 min, [M + H]$^+$ = 285. $^1$H-NMR (D$_6$-DMSO, 400 MHz) δ$_H$, 1.71-1.79 (m, 2H, CH$_2$CH$_2$CH$_2$), 2.34 (s, 3H, CCH$_3$), 2.56 (t, J = 6.4 Hz, 4H, CH$_2$CH$_2$CH$_2$), 2.77 (t, J = 8.0 Hz, 2H, CH$_2$CH$_2$N), 3.62 (s, 3H, NCH$_3$), 3.75 (t, J = 8.0 Hz, 2H, CH$_2$CH$_2$N), 6.97 (t, J = 8.0 Hz, 1H, C$_6$H$_4$), 7.04 (t, J = 8.0 Hz, 1H, C$_6$H$_4$), 7.30 (d, J = 8.0 Hz, 1H, C$_6$H$_4$), 7.48 (d, J = 8.0 Hz, 1H, C$_6$H$_4$). |

TABLE 3-continued

| Number of a compound | Structural formula | Constants |
|---|---|---|
| 50 | | LC/MS: an individual peak at a retention time of 1.15 min, [M + H]$^+$ = 284. $^1$H-NMR (D$_6$-DMSO, 400 MHz) δ$_H$, 1.77-1.84 (m, 2H, CH$_2$CH$_2$CH$_2$), 2.59 (t, J = 6.4 Hz, 4H, CH$_2$CH$_2$CH$_2$), 2.64 (t, J = 8.0 Hz, 2H, CH$_2$CH$_2$N), 3.85 (t, J = 8.0 Hz, 2H, CH$_2$CH$_2$N), 7.25 (t, J = 8.0 Hz, 1H, CH(Ph)), 7.45 (t, J = 8.0 Hz, 2H, CH(Ph)), 7.55 (s, 1H, CH(pyrazole)), 7.77 (d, J = 8.0 Hz, 2H, CH(Ph)), 8.28 (s, 1H, CH(pyrazole)). |
| 51 | | LC/MS: an individual peak at a retention time of 1.01 min, [M + H]$^+$ = 272. $^1$H-NMR (D$_6$-DMSO, 400 MHz) δ$_H$, 1.78-1.86 (m, 2H, CH$_2$CH$_2$CH$_2$), 2.56 (t, J = 6.4 Hz, 4H, CH$_2$CH$_2$CH$_2$), 3.01 (t, J = 8.0 Hz, 2H, CH$_2$CH$_2$N), 3.74 (s, 3H, CH$_3$), 4.05 (t, J = 8.0 Hz, 2H, CH$_2$CH$_2$N), 7.13 (t, J = 8.0 Hz, 1H, C$_6$H$_4$), 7.18 (t, J = 8.0 Hz, 1H, C$_6$H$_4$), 7.45 (d, J = 8.0 Hz, 1H, C$_6$H$_4$), 7.52 (d, J = 8.0 Hz, 1H, C$_6$H$_4$). |
| 52 | | LC/MS: an individual peak at a retention time of 1.24 min, [M + H]$^+$ = 286. $^1$H-NMR (D$_6$-DMSO, 400 MHz) δ$_H$, 1.79-1.87 (m, 2H, CH$_2$CH$_2$CH$_2$), 2.58 (t, J = 6.4 Hz, 4H, CH$_2$CH$_2$CH$_2$), 3.16 (t, J = 7.2 Hz, 2H, CH$_2$CH$_2$N), 4.07 (t, J = 7.2 Hz, 2H, CH$_2$CH$_2$N), 7.51-7.58 (m, 3H, CH(Ph)), 7.97 (dd, J = 8.0, 1.6 Hz, 2H, CH(Ph)). |
| 53 | | LC/MS: an individual peak at a retention time of 0.94 min, [M + H]$^+$ = 209. $^1$H-NMR (D$_6$-DMSO, 400 MHz) δ$_H$, 1.76-1.83 (m, 2H, CH$_2$CH$_2$CH$_2$), 2.53 (t, J = 6.4 Hz, 4H, CH$_2$CH$_2$CH$_2$), 4.00 (t, J = 6.4 Hz, 2H, NCH$_2$CH$_2$N), 4.27 (t, J = 6,4 Hz, 2H, NCH$_2$CH$_2$N), 7.86 (s, 1H, CH(triazole)), 8.43 (s, 1H, CH(triazole)). |
| 54 | | [M + H] = 255. $^1$H-NMR (400.13 MHz, DMSO-d$_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 2.82 (t, 2H, CCH$_2$CH$_2$N, J = 8.8 Hz); 3.89 (t, 2H, CCH$_2$CH$_2$N, J = 8.8 Hz); 6.91 (d, 1H, Indole-6, J = 9.0 Hz); 7.16 (s, 1H, NHCHC); 7.22 (s, 1H, Indole-4); 7.34 (d, 1H, Indole-7, J = 9.0 Hz); 10.75 (s, 1H, NH) |

TABLE 3-continued

| Number of a compound | Structural formula | Constants |
|---|---|---|
| 55 | (2-(1-methylpyrrolidin-2-yl)ethyl)-glutarimide structure | [M + H]⁺ = 225. 1H-NMR (400.13 MHz, DMSO-d₆, δ, m.d., J/Hz): 1.60 (dt, 2H, CHCH₂CH₂NC, J = 7.3 Hz, J = 7.1 Hz); 1.83 (t, 2H, CH₃NCH₂CH₂CH₂, J = 6.4 Hz); 1.84 (quint, 2H, CH₂CH₂CH₂, J = 7.5 Hz); 2.06 (m, 2H, CH₂CHCH₂CH₂N); 2.36 (s, 3H, CH₃); 2.68 (t, 4H, CH₂CH₂CH₂, J = 7.5 Hz); 3.06 (t, 2H, CH₃NCH₂, J = 6.4 Hz); 3.44 (quint, 1H, CH, J = 7.0 Hz); 3.68 (t, 2H, CHCH₂CH₂NC, J = 7.1 Hz) |
| 56 | 3-methyl-N-(2-(1H-imidazol-5-yl)ethyl)-glutarimide structure | [M + H]⁺ = 222. ¹H-NMR (400.13 MHz, DMSO-d₆, δ, m.d., J/Hz): 1.03 (d, 3H, CH₃, J = 6.7 Hz); 1.69 (dt, 2H, CH₂CH₂CHCH₃, J = 8.5 Hz, J = 7.5 Hz); 2.12 (tq, 1H, CNCCHCH₃, J = 8.5 Hz, J = 6.7 Hz); 2.54 (t, 2H, CH₂CH₂CHCH₃, J = 7.5 Hz); 3.20 (t, 2H, CCH₂CH₂NC, J = 7.0 Hz); 3.93 (t, 2H, CCH₂CH₂NC, J = 7.0 Hz); 6.86 (s, 1H, NHCHC); 7.56 (s, 1H, NH); 7.61 (s, 1H, NCHNH) |
| 57 | N-(2-(4,5-dihydro-1H-imidazol-4-yl)ethyl)-glutarimide structure | [M + H]⁺ = 210. ¹H-NMR (400.13 MHz, DMSO-d₆, δ, m.d., J/Hz): 1.60 (dt, 2H, NCHCH₂CH₂N, J = 11.2 Hz, J = 8.0 Hz); 1.84 (quint, 2H, CH₂CH₂CH₂, J = 7.5 Hz); 2.68 (t, 4H, CH₂CH₂CH₂, J = 7.5 Hz); 3.67 (d, 1H, NCHCH₂NH, J = 7.5 Hz); 3.68 (t, 1H, NCHCH₂CH₂N, J = 8.0 Hz); 4.05 (tt, 1H, NCHCH₂CH₂N, J = 7.5 Hz, J = 11.2 Hz); 8.31 (s, 1H, NCH); 8.73 (s, 1H, NH) |
| 58 | N-(2-(9H-purin-8-yl)ethyl)-glutarimide structure | [M + H]⁺ = 260. ¹H-NMR (400.13 MHz, DMSO-d₆, δ, m.d., J/Hz): 1.84 (quint, 2H, CCH₂CH₂CH₂, J = 7.5 Hz); 2.68 (t, 4H, CCH₂CH₂CH₂, J = 7.5 Hz); 2.94 (t, 2H, CCH₂CH₂NC, J = 7.2 Hz); 3.93 (t, 2H, CCH₂CH₂NC, J = 7.2 Hz); 8.90 (s, 1H, NCHN); 9.08 (s, 1H, NCHC); 13.60 (s, 1H, NH) |
| 59 | N-(2-(9H-purin-6-yl)ethyl)-glutarimide structure | [M + H]⁺ = 260. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 3.20 (t, 2H, CCH₂CH₂NC, J = 7.0 Hz); 3.93 (t, 2H, CCH₂CH₂NC, J = 7.0 Hz); 8.55 (s, 1H, NHCHN); 8.79 (s, 1H, NCHNC); 12.91 (s, 1H, NH) |
| 60 | N-(2-(9H-purin-2-yl)ethyl)-glutarimide structure | [M + H]⁺ = 260. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 2.94 (t, 2H, CCH₂CH₂NC, J = 7.2 Hz); 3.93 (t, 2H, CCH₂CH₂NC, J = 7.2 Hz); 8.67 (s, 1H, NHCHN); 8.95 (s, 1H, NHCCHNC); 12.55 (s, 1H, NH) |

TABLE 3-continued

| Number of a compound | Structural formula | Constants |
|---|---|---|
| 61 | | [M + H]⁺ = 272. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CCH₂CH₂CH₂, J = 7.5 Hz); 2.94 (t, 2H, NCH₂CH₂CN, J = 7.2 Hz); 3.93 (t, 2H, NCH₂CH₂CN, J = 7.2 Hz); 8.94 (s, 2H, NCHCHN); 8.95 (s, 1H, NCHCCN); 8.98 (s, 1H, NCHCHN) |
| 62 | | [M + H]⁺ = 272. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 3.20 (t, 2H, NCH₂CH₂CN, J = 7.0 Hz); 3.93 (t, 2H, NCH₂CH₂CN, J = 7.0 Hz); 8.75 (s, 1H, CCHN); 8.90 (s, 1H, NCHN); 9.08 (s, 1H, NCCCHN) |
| 63 | | [M + H]⁺ = 272. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 3.20 (t, 2H, NCH₂CH₂CN, J = 7.0 Hz); 8.60 (s, 1H, NCNCHCH); 8.79 (s, 1H, CNCHN); 8.98 (s, 1H, NCNCHCH) |
| 64 | | [M + H]⁺ = 191. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 2.95 (t, 2H, CCH₂CH₂NC, J = 6.6 Hz); 3.89 (t, 2H, CCH₂CH₂NC, J = 6.6 Hz); 7.72 (s, 1H, SCHC); 8.11 (s, 1H, NCHC) |
| 65 | | [M + H]⁺ = 223. ¹H-NMR (400.13 MHz, DMSO-d₆, δ, m.d., J/Hz): 2.53 (d, 4H, CCH₂CHNH₂, J = 7.5 Hz); 3.20 (t, 2H, CCH₂CH₂NC, J = 7.0 Hz); 3.89 (t, 1H, NCCH₂CHNH₂); 3.91 (bs, 2H, NH₂); 3.93 (t, 2H, CCH₂CH₂NC, J = 7.0 Hz); 6.86 (s, 1H, NHCHC); 7.56 (bs, 1H, NH); 7.61 (s, 1H, NCHNH) |
| 66 | | [M + H]⁺ = 251. ¹H-NMR (400.13 MHz, DMSO-d₆, δ, m.d., J/Hz): 1.53 (s, 5H, CHCHCH₂CH₂N); 1.54 (q, 4H, NCH₂CH₂CH, J = 8.3 Hz); 1.77 (td, 2H, CHCH₂CH₂N, J = 7.0 Hz, J = 6.0 Hz); 1.84 (quint, 2H, CCH₂CH₂CH₂, J = 7.5 Hz); 2.04 (m, 1H, CH₂CHCH₂CH₂N); 2.68 (t, 4H, CH₂CH₂CH₂, J = 7.5 Hz); 2.76 (d, 2H, NCH₂CHCH₂CH₂N, J = 8.2 Hz); 2.97 (t, 4H, NCH₂CH₂CHCH, J = 8.3 Hz); 3.68 (t, 2H, CH₂CHCH₂CH₂N, J = 7.0 Hz) |

TABLE 3-continued

| Number of a compound | Structural formula | Constants |
|---|---|---|
| 67 | | [M + H]⁺ = 223. ¹H-NMR (400.13 MHz, DMSO-d₆, δ, m.d., J/Hz): 1.70 (dt, 2H, CH₂CH₂CHNH₂, J = 12.0 Hz, J = 12.5 Hz); 2.48 (t, 2H, CH₂CH₂CHNH₂, J = 12.5 Hz); 3.20 (t, 2H, CCH₂CH₂NC, J = 7.0 Hz); 3.93 (t, 2H, CCH₂CH₂NC, J = 7.0 Hz); 3.97 (s, 2H, NH₂); 5.98 (t, 1H, CNCCHNH₂, J = 12.0 Hz); 6.86 (s, 1H, NCHC); 7.61 (s, 1H, NCHNH); 8.24 (s, 1H, NH) |
| 68 | | [M + H]⁺ = 279. ¹H-NMR (400.13 MHz, DMSO-d₆, δ, m.d., J/Hz): 1.01 (s, 6H, CH₃); 2.52 (s, 4H, CH₂CCH₂); 3.20 (t, 2H, CCH₂CH₂NC, J = 7.0 Hz); 4.15 (t, 1H, CCH₂CH₂NC, J = 7.0 Hz); 6.86 (s, 1H, NCHC); 7.61 (s, 1H, NCHNH); 8.24 (s, 1H, NH); 10.01 (s, 1H, OH) |
| 69 | | [M + H]⁺ = 279. ¹H-NMR (400.13 MHz, DMSO-d₆, δ, m.d., J/Hz): 0.85 (s, 3H, CH₃); 1.19 (s, 3H, CH₃); 1.69 (t, 2H, CH₂CH₂CCH₃, J = 7.5 Hz); 2.48 (t, 2H, CH₂CH₂CCH₃, J = 7.5 Hz); 3.20 (t, 2H, CCH₂CH₂N, J = 7.0 Hz); 4.15 (t, 1H, CCH₂CHNC, J = 7.0 Hz); 6.86 (s, 1H, NCHC); 7.61 (s, 1H, NCHNH); 8.24 (s, 1H, NH); 10.01 (s, 1H, OH) |
| 70 | | [M + H]⁺ = 266. ¹H-NMR (400.13 MHz, DMSO-d₆, δ, m.d., J/Hz): 1.03 (d, 3H, CH₃, J = 6.7 Hz); 1.69 (dt, 2H, CH₂CH₂CHCH₃, J = 8.5 Hz, J = 7.5 Hz); 2.12 (tq, 1H, CCHCH₃, J = 8.5 Hz, J = 6.7 Hz); 2.54 (t, 2H, CH₂CNCHC, J = 7.5 Hz); 2.56 (d, 2H, CCH₂CHCOH, J = 12.1 Hz); 4.16 (t, 1H, CH₂CNCHC, J = 12.1 Hz); 6.79 (s, 1H, NCHC); 8.03 (s, 1H, NCHNH); 8.26 (s, 1H, NH); 10.01 (s, 1H, OH) |
| 71 | | [M + H]⁺ = 266. ¹H-NMR (400.13 MHz, DMSO-d₆, δ, m.d., J/Hz): 0.86 (d, 3H, CH₃, J = 6.2 Hz); 1.90 (m, 1H, NCCH₂CHCH₃); 2.52 (d, 4H, CH₂CHCH₂, J = 7.5 Hz); 2.56 (d, 2H, CCH₂CHCOOH, J = 12.1 Hz); 4.16 (t, 1H, CNCHCOH, J = 12.1 Hz); 6.79 (s, 1H, NCHC); 8.03 (s, 1H, NCHNH); 8.26 (s, 1H, NH); 10.01 (s, 1H, OH) |
| 72 | | [M + H]⁺ = 252. ¹H-NMR (400.13 MHz, DMSO-d₆, δ, m.d., J/Hz): 1.84 (t, 2H, CH₂CH₂CH₂, J = 7.5 Hz); 2.68 (t, 4H, CH₂CH₂CH₂, J = 7.5 Hz); 3.20 (s, 2H, CCH₂CH₂N); 3.93 (s, 2H, CCH₂CH₂N); 8.03 (s, 1H, CH); 8.50 (s, 1H, NH); 11.18 (bs, 1H, OH) |

TABLE 3-continued

| Number of a compound | Structural formula | Constants |
|---|---|---|
| 73 | | [M + H]$^+$ = 222. $^1$H-NMR (400.13 MHz, DMSO-d$_6$, δ, m.d., J/Hz): 1.84 (quint, 2H, CH$_2$CH$_2$CH$_2$, J = 7.5 Hz); 2.47 (s, 3H, CH$_3$); 2.68 (t, 4H, CH$_2$CH$_2$CH$_2$, J = 7.5 Hz); 3.20 (t, 2H, CCH$_2$CH$_2$NC, J = 7.0 Hz); 3.93 (t, 2H, CCH$_2$CH$_2$NC, J = 7.0 Hz); 6.45 (s, 1H, CH); 11.70 (s, 1H, NH) |
| 74 | | [M + H]$^+$ = 284. $^1$H-NMR (400.13 MHz, DMSO-d$_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 3.20 (t, 2H, CCH$_2$CH$_2$NC, J = 7.0 Hz); 3.93 (t, 2H, CCH$_2$CH$_2$NC, J = 7.0 Hz); 6.87 (s, 1H, NCHC); 7.60 (dd, 2H, m-Ph, J = 7.8 Hz, J = 7.4 Hz); 7.62 (d, 1H, p-Ph, J = 7.4 Hz); 8.31 (d, 2H, o-Ph, J = 7.8 Hz); 11.45 (s, 1H, N$\underline{H}$) |
| 75 | | [M + H]$^+$ = 267. $^1$H-NMR (400.13 MHz, DMSO-d$_6$, δ, m.d., J/Hz): 1.70 (m, 2H, CH$_2$CH$_2$CHNH$_2$); 2.48 (t, 2H, CH$_2$CNCHC, J = 12.5 Hz); 2.56 (d, 2H, CCH$_2$CHCOOH, J = 12.1 Hz); 3.97 (s, 2H, NH$_2$); 4.16 (t, 1H, CH$_2$CNCHC, J = 12.1 Hz); 5.98 (t, 1H, CNCCHNH$_2$, J = 12.0 Hz); 6.79 (s, 1H, NHCHC); 7.56 (s, 1H, NH); 8.03 (s, 1H, NCHNH); 10.01 (s, 1H, OH) |
| 76 | | [M + H] = 268. $^1$H-NMR (400.13 MHz, DMSO-d$_6$, δ, m.d., J/Hz): 1.67 (t, 2H, CH$_2$CH$_2$CHOH, J = 8.4 Hz); 2.48 (t, 2H, CH$_2$CNCHC, J = 12.5 Hz); 2.56 (d, 2H, CCH$_2$CHCOH, J = 12.1 Hz); 4.16 (t, 1H, CH$_2$CNCHC, J = 12.1 Hz); 4.60 (t, 1H, CNCCHOH, J = 8.4 Hz); 5.38 (s, 1H, OH); 6.79 (s, 1H, NCHC); 8.03 (s, 1H, NCHNH); 8.26 (s, 1H, NH); 10.01 (s, 1H, COOH) |
| 77 | | [M + H]$^+$ = 234. $^1$H-NMR (400.13 MHz, DMSO-d$_6$, δ, m.d., J/Hz): 1.84 (quint, 2H, CH$_2$CH$_2$CH$_2$, J = 7.5 Hz); 2.65 (t, 4H, CH$_2$CH$_2$CH$_2$ J = 7.5 Hz); 3.03 (d, 2H, CCH$_2$CHCOOH, J = 10.5 Hz); 4.16 (t, 1H, NCHCH$_2$, J = 10.5 Hz); 6.84 (d, 1H, SCCH, J = 3.4 Hz); 6.97 (dd, 1H, SCHCH, J = 5.0 Hz); 7.39 (d, 1H, SCHCH, J = 5.0 Hz); 10.01 (bs, 1H, OH) |
| 78 | | [M + H]$^+$ = 248. $^1$H-NMR (400.13 MHz, DMSO-d$_6$, δ, m.d., J/Hz): 1.84 (quint, 2H, CCH$_2$CH$_2$CH$_2$, J = 7.5 Hz); 2.65 (t, 4H, CH$_2$CH$_2$CH$_2$ J = 7.5 Hz); 3.03 (d, 2H, SCCH$_2$CHC, J = 10.5 Hz); 3.67 (s, 3H, CH$_3$); 4.16 (t, 1H, NCHCOCH$_3$, J = 10.5 Hz); 6.84 (d, 1H, SCCH, J = 3.4 Hz); 6.97 (dd, 1H, SCHCHCH, J = 5.0 Hz, J = 3.4 Hz); 7.39 (d, 1H, SCH, J = 5.0 Hz) |

TABLE 3-continued

| Number of a compound | Structural formula | Constants |
|---|---|---|
| 79 | | [M + H]⁺ = 192. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 3.20 (t, 2H, CCH₂CH₂N, J = 7.0 Hz); 3.93 (t, 2H, CCH₂CH₂N, J = 7.0 Hz); 7.76 (s, 1H, CH) |
| 80 | | [M + H]⁺ = 220. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 2.95 (t, 2H, NCH₂CH₂C, J = 6.6 Hz); 3.89 (t, 2H, NCH₂CH₂C, J = 6.6 Hz); 8.32 (s, 2H, CH₂CCH); 8.97 (s, 1H, NCHN) |
| 81 | | [M + H]⁺ = 220. ¹H-NMR (400.13 MHz, DMSO-d₆, δ, m.d., J/Hz): 1.84 (quint, 2H, CCH₂CH₂CH₂, J = 7.5 Hz); 2.68 (t, 4H, CCH₂CH₂CH₂, CCH₂CH₂CH₂, J = 7.5 Hz); 2.95 (t, 2H, CNCH₂CH₂C, J = 8.1 Hz); 3.89 (t, 2H, CNCH₂CH₂C, J = 8.1 Hz); 7.38 (d, 1H, CCHCHN, J = 5.0 Hz); 9.20 (d, 1H, CCHCHN, J = 5.0 Hz); 9.28 (s, 1H, CCHN) |
| 82 | | [M + H]⁺ = 235. ¹H-NMR (400.13 MHz, DMSO-d₆, δ, m.d., J/Hz): 1.84 (quint, 2H, CH₂CH₂CH₂, J = 7.5 Hz); 2.65 (t, 4H, CH₂CH₂CH₂, J = 7.5 Hz); 2.74 (d, 2H, CCH₂CHCOOH, J = 12.1 Hz); 4.16 (t, 1H, NCHCH₂C, J = 12.1 Hz); 7.22 (s, 1H, SCHC); 8.98 (s, 1H, SCHN); 10.01 (bs, 1H, OH) |
| 83 | | [M + H]⁺ = 263. ¹H-NMR (400.13 MHz, DMSO-d₆, δ, m.d., J/Hz): 1.84 (quint, 2H, CH₂CH₂CH₂, J = 7.5 Hz); 2.65 (t, 4H, CH₂CH₂CH₂, J = 7.5 Hz); 2.74 (d, 2H, CCH₂CHCOOH, J = 12.1 Hz); 4.16 (t, 1H, NCHCOOH, J = 12.1 Hz); 7.23 (dd, 1H, NCHCHCH, J = 4.7 Hz, J = 7.5 Hz); 7.29 (d, 1H, NCCH, J = 7.8 Hz); 7.66 (dd, 1H, NCHCHCH, J = 7.5 Hz, J = 7.8 Hz); 8.62 (d, 1H, NCHCHCH, J = 4.7 Hz); 10.01 (bs, 1H, OH) |
| 84 | | [M + H]⁺ = 234. ¹H-NMR (400.13 MHz, DMSO-d₆, δ, m.d., J/Hz): 1.84 (quint, 2H, CH₂CH₂CH₂, J = 7.5 Hz); 2.65 (t, 4H, CH₂CH₂CH₂, J = 7.5 Hz); 3.09 (d, 2H, CCH₂CHCOH, J = 11.7 Hz); 4.16 (t, 1H, NCHCH₂C, J = 11.7 Hz); 7.12 (d, 1H, SCHCH, J = 4.8 Hz); 7.40 (d, 1H, SCHCH, J = 4.8 Hz); 7.46 (s, 1H, SCHC); 10.01 (bs, 1H, OH) |

TABLE 3-continued

| Number of a compound | Structural formula | Constants |
|---|---|---|
| 85 | | [M + H]$^+$ = 252. $^1$H-NMR (400.13 MHz, DMSO-d$_6$, δ, m.d., J/Hz): 1.84 (quint, 2H, CH$_2$CH$_2$CH$_2$, J = 7.5 Hz); 2.65 (t, 4H, CH$_2$CH$_2$CH$_2$, J = 7.5 Hz); 2.99 (d, 2H, CCH$_2$CHCOOH, J = 10.5 Hz); 4.16 (t, 1H, CNCHCH$_2$, J = 10.5 Hz); 6.37 (d, 2H, OCHCHCH, J = 3.0 Hz); 7.39 (s, 1H, OCH); 10.01 (bs, 1H, OH) |
| 86 | | LC/MS: an individual peak at a retention time of 1.01 min, [M]$^+$ = 238. $^1$H-NMR (D$_6$-DMSO, 400 MHz) δ$_H$, 1.79-1.86 (m, 2H, CH$_2$CH$_2$CH$_2$), 2.30 (s, 3H, CH$_3$), 2.57 (t, J = 6,4 Hz, 4H, CH$_2$CH$_2$CH$_2$), 3.04 (t, J = 7.5 Hz, 2H, CH$_2$CH$_2$N), 3.94 (t, J = 7.5 Hz, 2H, CH$_2$CH$_2$N), 7.06 (s, 1H, CH(thiazole)). |
| 87 | | [M + H]$^+$ = 222. $^1$H-NMR (400.13 MHz, DMSO-d$_6$, δ, m.d., J/Hz): 1.84 (quint, 2H, CH$_2$CH$_2$CH$_2$, J = 7.5 Hz); 2.46 (s, 3H, CH$_3$); 2.68 (t, 4H, CH$_2$CH$_2$CH$_2$, J = 7.5 Hz); 4.08 (t, 2H, CNCH$_2$CH$_2$N, J = 5.8 Hz); 4.50 (t, 2H, CNCH$_2$CH$_2$N, J = 5.8 Hz); 7.26 (s, 1H, CHNCH$_2$CH$_2$N); 7.49 (s, 1H, CHNCCH$_3$) |
| 88 | | [M + H]$^+$ = 226. $^1$H-NMR (400.13 MHz, DMSO-d$_6$, δ, m.d., J/Hz): 1.60 (dt, 2H, CHCH$_2$CH$_2$NC, J = 9.2 Hz, J = 7.1 Hz); 1.84 (quint, 2H, CH$_2$CH$_2$CH$_2$, J = 7.5 Hz); 2.10 (bs, 1H, NHCHCH$_2$CH$_2$N); 2.68 (t, 4H, CH$_2$CH$_2$CH$_2$, J = 7.5 Hz); 3.27 (t, 4H, NHCH$_2$CH$_2$NH, J = 7.5 Hz); 3.35 (d, 2H, NHCH$_2$CH, J = 9.9 Hz); 3.56 (m, 1H, CH); 3.68 (t, 2H, CHCH$_2$CH$_2$N, J = 7.1 Hz); 4.07 (bs, 1H, NHCH$_2$CH$_2$NH) |
| 89 | | LC/MS: an individual peak at a retention time of 1.01 min, [M]$^+$ = 227. $^1$H-NMR (400.13 MHz, DMSO-d$_6$, δ, m.d., J/Hz): 1.60 (m, 2H, morph), 1.80 (quint, 2H, COCH$_2$CH$_2$CH$_2$CO, J = 6.6 Hz), 2.60 (t, 4H, COCH$_2$CH$_2$CH$_2$CO, J = 6.6 Hz), 2.70 (m, 1H, morph), 2.90 (m, 1H, morph), 3.15 (m, 2H, CH$_2$CH), 3.65 (m, 3H, morph + CH$_2$N), 3.80 (m, 1H, morph), 3.85 (d, 1H, morph, J = 12.2 Hz), 9.45 (s, 3H, NH + HCl) |
| 90 | | LC/MS: an individual peak at a retention time of 0.21 min, [M + H]$^+$ = 227. $^1$H-NMR (400.13 MHz, DMSO-d$_6$, δ, m.d., J/Hz): 1.64 (m, 1H, morph), 1.75 (m, 1H, morph), 1.84 (quint, 2H, COCH$_2$CH$_2$CH$_2$CO, J = 6.6 Hz), 2.61 (t, 4H, COCH$_2$CH$_2$CH$_2$CO, J = 6.6 Hz), 3.02 (m, 1H, morph), 3.16 (m, 2H, CH$_2$CH), 3.47 (m, 1H, morph), 3.68 (m, 3H, morph + CH$_2$N), 3.86 (d, 1H, morph, J = 12.2 Hz), 3.99 (d, 1H, morph, J = 12.2 Hz), 9.45 (s, 3H, NH + HCl) |

TABLE 3-continued

| Number of a compound | Structural formula | Constants |
|---|---|---|
| 91 | 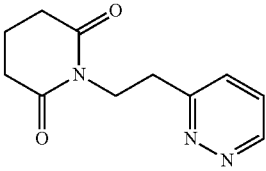 [SMILES: O=C1CCCC(=O)N1CCc1cccnn1] | $[M + H]^+ = 220$. $^1$H-NMR (400.13 MHz, DMSO-$d_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 3.20 (t, 2H, NCH$_2$CH$_2$C, J = 7.0 Hz); 3.93 (t, 2H, NCH$_2$CH$_2$C, J = 7.0 Hz); 7.35 (d, 1H, NCCH, J = 8.0 Hz); 7.77 (dd, 1H, NCHCHCH, J = 5.1 Hz, J = 8.0 Hz); 9.18 (d, 1H, NCHCHCH, J = 5.1 Hz) |
| 92 | 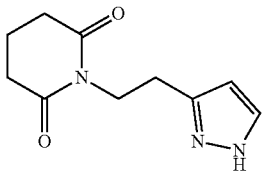 [SMILES: O=C1CCCC(=O)N1CCc1cc[nH]n1] | $[M + H]^+ = 208.11$ $^1$H-NMR (400.13 MHz, DMSO-$d_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 3.20 (t, 2H, CCH$_2$CH$_2$N, J = 7.0 Hz); 3.93 (t, 2H, CCH$_2$CH$_2$N, J = 7.0 Hz); 5.90 (s, 1H, NCCH); 7.30 (s, 1H, NNHCH); 12.06 (bs, 1H, NH) |
| 93 | 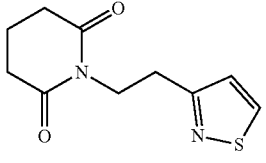 | $[M + H]^+ = 191$. $^1$H-NMR (400.13 MHz, DMSO-$d_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 3.20 (t, 2H, CCH$_2$CH$_2$N, J = 7.0 Hz); 3.93 (t, 2H, CCH$_2$CH$_2$N, J = 7.0 Hz); 6.91 (d, 1H, NCCH, J = 4.6 Hz); 7.72 (d, 1H, NSCH, J = 4.6 Hz) |
| 94 | 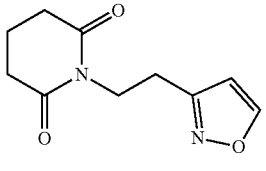 | $[M + H]^+ = 209$. $^1$H-NMR (400.13 MHz, DMSO-$d_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 3.20 (t, 2H, CCH$_2$CH$_2$N, J = 7.0 Hz); 3.93 (t, 2H, CCH$_2$CH$_2$N, J = 7.0 Hz); 6.80 (s, 1H, NCCH); 7.10 (s, 1H, NOCH) |
| 95 | 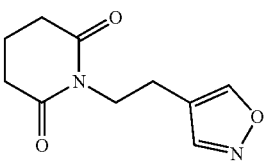 [SMILES: O=C1CCCC(=O)N1CCc1cnoc1] | $[M + H]^+ = 209$. $^1$H-NMR (400.13 MHz, DMSO-$d_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 2.95 (t, 2H, CCH$_2$CH$_2$N, J = 7.7 Hz); 3.89 (t, 2H, CCH$_2$CH$_2$N, J = 7.7 Hz); 8.38 (s, 1H, NCHC); 9.10 (s, 1H, NOCH) |
| 96 | 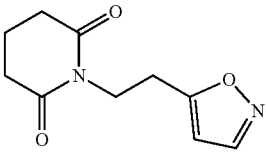 | $[M + H]^+ = 209$. $^1$H-NMR (400.13 MHz, DMSO-$d_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 2.94 (t, 2H, CCH$_2$CH$_2$N, J = 7.2 Hz); 3.93 (t, 2H, CCH$_2$CH$_2$N, J = 7.2 Hz); 6.29 (s, 1H, NOCCH); 8.39 (s, 1H, ONCH) |
| 97 | 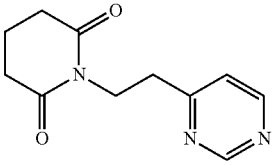 | $[M + H]^+ = 220$. $^1$H-NMR (400.13 MHz, DMSO-$d_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 3.20 (t, 2H, NCH$_2$CH$_2$C, J = 7.0 Hz); 3.93 (t, 2H, NCH$_2$CH$_2$C, J = 7.0 Hz); 6.42 (d, 1H, CCHCHN, J = 5.1 Hz); 8.73 (d, 1H, CCHCHN, J = 5.1 Hz); 9.03 (s, 1H, NCHN) |

TABLE 3-continued

| Number of a compound | Structural formula | Constants |
|---|---|---|
| 98 | | [M + H]$^+$ = 220. $^1$H-NMR (400.13 MHz, DMSO-d$_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 2.94 (t, 2H, NCH$_2$CH$_2$C, J = 7.2 Hz); 3.93 (t, 2H, NCH$_2$CH$_2$C, J = 7.2 Hz); 7.30 (d, 1H, CHCHCH, J = 5.2 Hz); 8.70 (d, 2H, CHCHCH, J = 5.2 Hz) |
| 99 | | [M + H] = 207. $^1$H-NMR (400.13 MHz, DMSO-d$_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 3.20 (t, 2H, NCH$_2$CH$_2$C, J = 7.0 Hz); 3.93 (t, 2H, NCH$_2$CH$_2$C, J = 7.0 Hz); 5.91 (d, 1H, CCHCHCH, J = 4.0 Hz); 6.07 (d, 1H, CCH, J = 4.0 Hz); 6.56 (s, 1H, NHCH); 11.21 (bs, 1H, NH) |
| 100 | | [M + H]$^+$ = 239. $^1$H-NMR (400.13 MHz, DMSO-d6, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 2.94 (t, 2H, CCH$_2$CH$_2$N, J = 7.2 Hz); 3.93 (t, 2H, CCH$_2$CH$_2$N, J = 7.2 Hz); 4.02 (s, 3H, CH$_3$); 7.02 (s, 1H, CH) |
| 101 | | [M + H]$^+$ = 204. $^1$H-NMR (400.13 MHz, DMSO-d$_6$, δ, m.d., J/Hz): 1.84 (quint, 2H, CCH$_2$CH$_2$CH$_2$C, J = 7.5 Hz); 2.00 (quint, 2H, CCH$_2$CH$_2$CH$_2$N, J = 7.4 Hz, J = 6.0 Hz); 2.68 (t, 4H, CCH$_2$CH$_2$CH$_2$C, J = 7.5 Hz); 2.94 (t, 2H, CCH$_2$CH$_2$CH$_2$N, J = 7.4 Hz); 3.68 (t, 2H, CCH$_2$CH$_2$CH$_2$N, J = 6.0 Hz); 6.91 (d, 1H, SCCH, J = 3.4 Hz); 6.96 (dd, 1H, CHCHCH, J = 5.0 Hz, J = 3.4 Hz); 7.36 (d, 1H, SCH, J = 5.0 Hz) |
| 102 | | [M + H]$^+$ = 233. $^1$H-NMR (400.13 MHz, DMSO-d$_6$, δ, m.d., J/Hz): 1.84 (quint, 2H, CCH$_2$CH$_2$CH$_2$C, J = 7.5 Hz); 2.00 (tt, 2H, NCH$_2$CH$_2$CH$_2$C, J = 6.0 Hz, J = 7.0 Hz); 2.68 (t, 4H, CH$_2$CH$_2$CH$_2$, J = 7.5 Hz); 2.77 (t, 2H, NCH$_2$CH$_2$CH$_2$C, J = 7.0 Hz); 3.68 (t, 2H, NCH$_2$CH$_2$CH$_2$C, J = 6.0 Hz); 7.23 (dd, 1H, CNCHCH, J = 4.7 Hz, J = 7.5 Hz); 7.29 (d, 1H, CCH, J = 7.8 Hz); 7.66 (dd, 1H, CCHCHCH, J = 7.5 Hz, J = 7.8 Hz); 8.62 (d, 1H, NCHCHCH, J = 4.7 Hz) |
| 103 | | [M + H]$^+$ = 253. $^1$H-NMR (400.13 MHz, DMSO-d$_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 2.95 (t, 2H, NCH$_2$CH$_2$C, J = 8.1 Hz); 3.89 (t, 2H, NCH$_2$CH$_2$C, J = 8.1 Hz); 7.39 (d, 1H, NCHCCH, J = 8.2 Hz); 7.57 (d, 1H, NCCH, J = 8.2 Hz); 8.32 (s, 1H, CCHN) |

TABLE 3-continued

| Number of a compound | Structural formula | Constants |
|---|---|---|
| 104 | | [M + H]⁺ = 243. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz), 2.94 (t, 2H, CCH₂CH₂N, J = 7.2 Hz); 3.93 (t, 2H,CCH₂CH₂N, J = 7.2 Hz); 7.02 (s, 1H, CH) |
| 105 | | [M + H]⁺ = 253. ¹H-NMR (400.13 MHz, DMSO-d₆, δ, m.d., J/Hz): 1.84 (quint, 2H, CCH₂CH₂CH₂C, J = 7.5 Hz); 2.00 (m, 2H, CCH₂CH₂CH₂N); 2.68 (t, 4H, CH₂CH₂CH₂, J = 7.5 Hz); 2.94 (t, 2H, CCH₂CH₂CH₂N, J = 7.4 Hz); 3.68 (t, 2H, CCH₂CH₂CH₂N, J = 6.0 Hz); 4.02 (s, 3H, CH₃); 7.02 (s, 1H, CH) |
| 106 | | [M + H]⁺ = 257. ¹H-NMR (400.13 MHz, DMSO-d₆, δ, m.d., J/Hz): 1.84 (quint, 2H, CCH₂CH₂CH₂C, J = 7.5 Hz); 2.00 (m, 2H, CCH₂CH₂CH₂N); 2.68 (t, 4H, CCH₂CH₂CH₂C, J = 7.5 Hz); 2.94 (t, 2H, CCH₂CH₂CH₂N, J = 7.4 Hz); 3.68 (t, 2H, CCH₂CH₂CH₂N, J = 6.0 Hz); 7.02 (s, 1H, CH) |
| 107 | | [M + H]⁺ = 257. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 3.20 (t, 2H, CCH₂CH₂N, J = 7.0 Hz); 3.93 (t, 2H, CCH₂CH₂N, J = 7.0 Hz); 6.40 (s, 1H, Indole-3); 7.26 (d, 1H, Indole-7, J = 7.9 Hz); 7.39 (m, 2H, Indole-4, Indole-6); 7.52 (dd, 1H, Indole-5, J = 7.4 Hz, J = 7.9 Hz); 10.80 (s, 1H, NH) |
| 108 | | [M + H]⁺ = 233. ¹H-NMR (400.13 MHz, DMSO-d₆, δ, m.d., J/Hz): 1.84 (quint, 2H, CCH₂CH₂CH₂C, J = 7.5 Hz); 2.00 (tt, 2H, NCH₂CH₂CH₂C, J = 6.0 Hz, J = 7.8 Hz); 2.38 (t, 2H, NCH₂CH₂CH₂C, J = 7.8 Hz); 2.68 (t, 4H, CCH₂CH₂CH₂C, J = 7.5 Hz); 3.68 (t, 2H, NCH₂CH₂CH₂C, J = 6.0 Hz); 7.49 (d, 2H, CCHCHN, J = 5.5 Hz); 8.64 (d, 2H, CCHCHN, J = 5.5 Hz) |
| 109 | | [M + H]⁺ = 249. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 2.95 (t, 2H, NCH₂CH₂C, J = 8.1 Hz); 3.89 (t, 2H, NCH₂CH₂C, J = 8.1 Hz); 3.94 (s, 3H, CH₃); 6.82 (d, 1H, CCHCHCN, J = 9.2 Hz); 7.39 (d, 1H, CCHCHCN, J = 9.2 Hz); 8.32 (s, 1H, CCHN) |
| 110 | | [M + H]⁺ = 191. ¹H-NMR (400.13 MHz, DMSO-d₆, δ, m.d., J/Hz): 1.84 (quint, 2H, CH₂CH₂CH₂, J = 7.5 Hz); 2.68 (t, 4H, CH₂CH₂CH₂, J = 7.5 Hz); 3.20 (t, 2H, CCH₂CH₂N, J = 7.0 Hz); 3.93 (t, 2H, CCH₂CH₂N, J = 7.0 Hz); 7.22 (s, 1H, SCHC); 8.98 (s, 1H, SCHN) |

TABLE 3-continued

| Number of a compound | Structural formula | Constants |
|---|---|---|
| 111 | | $[M + H]^+$ = 209. $^1$H-NMR (400.13 MHz, DMSO-$d_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 2.94 (t, 2H, CCH$_2$CH$_2$N, J = 7.2 Hz); 3.93 (t, 2H, CCH$_2$CH$_2$N, J = 7.2 Hz); 7.76 (s, 1H, NCHC); 8.84 (s, 1H, CHOC) |
| 112 | | $[M + H]^+$ = 208. $^1$H-NMR (400.13 MHz, DMSO-$d_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 2.95 (t, 2H, CCH$_2$CH$_2$N, J = 6.6 Hz); 3.89 (t, 2H, CCH$_2$CH$_2$N, J = 6.6 Hz); 7.63 (s, 2H, NCHC); 12.61 (bs, 1H, NH) |
| 113 | | $[M + H]^+$ = 220. $^1$H-NMR (400.13 MHz, DMSO-$d_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 3.20 (t, 2H, NCH$_2$CH$_2$C, J = 7.0 Hz); 3.93 (t, 2H, NCH$_2$CH$_2$C, J = 7.0 Hz); 7.91 (s, 1H, CNCHCHN); 8.71 (s, 1H, CNCHCHN); 8.75 (s, 1H, CCHN) |
| 114 | | $[M + H]^+$ = 258. $^1$H-NMR (400.13 MHz, DMSO-$d_6$, δ, m.d., J/Hz): 1.84 (quint, 2H, CH$_2$CH$_2$CH$_2$, J = 7.5 Hz); 2.68 (t, 4H, CH$_2$CH$_2$CH$_2$, J = 7.5 Hz); 3.20 (t, 2H, CCH$_2$CH$_2$N, J = 7.0 Hz); 3.93 (t, 2H, CCH$_2$CH$_2$N, J = 7.0 Hz); 6.78 (dd, 1H, CCHNCHCH, J = 6.8 Hz, J = 7.0 Hz); 7.18 (dd, 1H, CCHNCHCHCH, J = 9.0 Hz, J = 6.8 Hz); 7.43 (d, 1H, CNCCH, J = 9.0 Hz); 7.68 (s, 1H, CCHN); 8.43 (d, 1H, CCNCH, J = 7.0 Hz) |
| 115 | | $[M + H]^+$ = 194. $^1$H-NMR (400.13 MHz, DMSO-$d_6$, δ, m.d., J/Hz): 1.84 (quint, 2H, CH$_2$CH$_2$CH$_2$, J = 7.5 Hz); 2.65 (t, 4H, CH$_2$CH$_2$CH$_2$, J = 7.5 Hz); 5.36 (s, 2H, CCH$_2$N); 6.87 (s, 1H, NCHC); 7.79 (s, 1H, NCHNH); 8.50 (s, 1H, NH) |

Example 10

Assessment of the Efficiency of Compounds in an Acute Rhinosinusitis Rat Model

Morphological studies of histologic preparations were conducted with a Leica DMLS light-optical microscope (Leica Microsystems, Germany). Micro-morphometric assessment was performed by using an ocular micrometer on a Leica DMLB microscope.

Acute rhinosinusitis was induced by intranasal administration of 20 μl of 7.5% formalin solution (aqueous solution comprising 40% formaldehyde, 8% methyl alcohol, and 52% water) to each nasal passage of rats.

Administration of formalin to rat nasal passages leads to the dissemination of inflammation to adjacent tissues, resulting in a clinical pattern similar to the symptoms of rhinosinusitis in a human.

After an acclimatization period, the following groups were formed:

- intact animals administered intragastrically a saline solution in an amount of 0.2 ml, the induction of acute rhinosinusitis was not performed;
- a control group consisted of the animals administered intragastrically a saline solution in an amount of 0.2 ml for 7 days after induction of acute rhinosinusitis;
- animals administered intramuscularly dexamethasone at a dose of 0.33 mg/kg for 7 days after induction of acute rhinosinusitis; and
- animals administered the tested compounds at a dose of 27 mg/kg for 7 days after induction of acute rhinosinusitis.

Clinical observation of each animal was performed every day at least twice daily.

In the experiment with Wistar rats, the induction of acute rhinosinusitis by administration of a 7.5% formalin solution to nasal passages caused in the control group of animals pronounced pathological changes characterizing the development of an acute inflammation process in the nasal mucous. The caused pathology was characterized by congestion, hyperplasia, focal necrosis of the nasal meatus mucous membrane, an increased number of caliciform cells, pronounced infiltration by mononuclear cells and leucocytes, and mucus hyperproduction by submucosal glands.

The mucous and submucous membranes of both nasal passages (respiratory and olfactory regions) of the experimental animals were subjected to a morphological analysis to evaluate a specific activity of the compounds.

After completion of the clinical phase of the experiment, the material derived from the animals (nose, nasolabial triangle) was dissected out and fixed in a 10% formalin solution for 24 hours and then decalcified in a 12% "De Castro" solution, after that the material was subjected to a standard treatment in alcohols with progressively increasing concentrations (70-95%), xylene and paraffin to produce histologic preparations with a thickness of serial paraffin sections of 3-5 μm. For microscopic examination, the sections were stained with hematoxylin and eosin. Detection of acid mukopolysaccharides, the production of which is increased in an inflammation, was performed by histochemical staining of the preparation with Alcian Blue (pH 2.5). The comparison and histological evaluation of changes were performed versus the group of intact rats.

After slaughter, the gross appearance of inflammation in the nasal passages was studied in each animal. Histological, hystochemical and morphological studies of rats were intended to evaluate the following characteristics of nasal passages: congestion of the mucous membrane; hyperplasia and necrosis of nasal epithelium, the number of caliciform cells within 1 mm of the mucous membrane of the nasal septum, and the character of inflammation.

In this study, the efficiency of the mucociliary system was evaluated by the number of caliciform cells and, as a consequence, microscopic changes in the mucous membrane of the nasal passages.

Table 4.

The number of caliciform cells within 1 mm of the mucous membrane of the nasal septum

TABLE 4

The number of caliciform cells within 1 mm of the mucous membrane of the nasal septum in rats, M ± m (data of several experiments)

| Group | N | The number of caliciform cells |
|---|---|---|
| Intact | 58 | 24.4 ± 0.7 |
| Control | 58 | 43.3 ± 0.6 |
| Dexamethasone | 6 | 34.8 ± 2.1* |
| Compound 1 | 18 | 31.2 ± 1.2* |
| Compound 3 | 12 | 35.8 ± 0.9* |
| Compound 6 | 6 | 36.5 ± 0.8* |
| Compound 8 | 6 | 34.5 ± 0.8* |
| Compound 124 | 12 | 37.6 ± 1.4* | n is the number of animals,
*$p < 0.05$ vs. control
n is the number of animals

TABLE 5

Macroscopic characteristic of changes in the mucous membrane of nasal passages in rats of different groups (data of several experiments)

| Group | n | Without changes | Muculent or mucopurulent catarrh |
|---|---|---|---|
| Intact | 58 | 58 | 0 |
| Control | 58 | 0 | 58 |
| Dexamethasone | 6 | 3 | 3 |
| Compound 1 | 18 | 5 | 13 |
| Compound 3 | 12 | 5 | 7 |
| Compound 6 | 6 | 2 | 4 |
| Compound 7 | 18 | 5 | 13 |
| Compound 8 | 6 | 3 | 3 |
| Compound 124 | 12 | 4 | 8 |
| Compound 20 | 8 | 4 | 4 |
| Compound 2 | 8 | 5 | 3 |
| Compound 28 | 8 | 4 | 4 |
| Compound 76 | 8 | 2 | 6 |
| Compound 56 | 8 | 5 | 3 |
| Compound 65 | 8 | 4 | 4 |
| Compound 75 | 8 | 3 | 5 |
| Compound 70 | 8 | 4 | 4 |
| Compound 21 | 8 | 3 | 5 |
| Compound 27 | 8 | 4 | 4 |
| Compound 32 | 8 | 3 | 5 |
| Compound 33 | 8 | 3 | 5 |
| Compound 44 | 8 | 4 | 4 | n is the number of animals

As can be seen from tables 4 and 5, the compounds of general formula I (without any limitation to the studied compounds) effectively maintain the efficiency of the mucociliary system and show therapeutic efficiency in the rhinosinusitis model. The pharmacological action of the studied compounds was expressed in more pronounced regeneration of the epithelium, a reduction in the number of caliciform cells and mucus hypersecretion.

Example 11

Antiviral Activity of Compounds of Formula (I) Against Coxsackie Virus In Vivo

The study used trypsin-dependent strain HCXV A2 previously adapted and causing death of mice from Coxsackie virus infection.

The experiment was carried out by using white mice weighed 6 to 7 g. The animals were infected intramuscularly with a dose of 0.1 ml/mouse. The infectious dose used in the experiment was $10LD_{50}$ causing lethality in mice.

The ability of the compounds to provide a therapeutic effect was evaluated by the mortality rate in HCXV A2 virus-infected mice in the control group, relative to the untreated group of mice.

The studied compounds and placebo were administered orally according to the treatment scheme. The placebo administered to mice consisted of a line solution. Intact animals served as a negative control were hold under the same conditions as the experimental animals, in separate rooms.

The animals used in the experiment were divided into groups by 14-15 animals. Compounds were administered at a dose of 30 mg/kg of body weight. The studied compounds were administered orally once daily for 7 days (first administration was performed at 24 hours after the infection). The animals were monitored for 15 days, during which the animals were weighed every day and the mortality rate was registered.

During the study of the effectiveness of the tested compounds in HCXV A2 virus infection, non-specific fatal cases were not registered in the control group of intact animals.

Compounds of general formula (I) had a protective effect against the experimental Coxsackie virus infection by decreasing the mortality rate among the animals and increasing their average-expectancy life. Data of some particular compounds of formula (I) (without any limitation to the recited compounds) are represented in the table (Table 6).

The described antiviral activity of the tested compounds demonstrates that these chemical compounds may be used as effective medicaments in HCXV enterovirus infection.

mouse lungs by measuring a viral titer in the experimental groups versus the control group on days 5 and 7 after infection.

The results of measuring the weight of animals for some particular compounds of formula (I) (without any limitation to the recited compounds) are represented in the table 7. The virus control group had a statistically significant weight loss in the mice, compared to the intact animals. The antiviral activity of the compounds of general formula (I) was evident in a body weight gain of the mice, compared to the control animals.

TABLE 6

Efficiency of the compounds of general formula (I) against Coxsackie A2-virus infection in the mice model.

| Tested compounds | Dose of tested compounds and reference preparation mg/kg | Total number of animals in a group | Total mortality rate, % | Average expectancy life (days) Relative | Vs. control | Protective index (%) |
|---|---|---|---|---|---|---|
| Compound 12 | 30 | 15 | 40.0 | 24.9 | +14.2 | 45 |
| Compound 13 | 30 | 15 | 46.7 | 19.0 | +8.3 | 36 |
| Compound 14 | 30 | 15 | 50.0 | 21.4 | +10.4 | 36 |
| Compound 23 | 30 | 15 | 50.0 | 23.8 | +13.1 | 36 |
| Compound 30 | 30 | 15 | 60.0 | 13.1 | +2.4 | 18 |
| Compound 35 | 30 | 15 | 53.3 | 16.6 | +5.9 | 27 |
| Compound 36 | 30 | 15 | 53.3 | 16.7 | +6.0 | 27 |
| Compound 89 | 30 | 15 | 53.3 | 17.7 | +7.0 | 27 |
| Virus control |  | 15 | 73.3 | 10.7 |  |  |
| Compound 90 | 30 | 14 | 35.7 | 25.9 | +15.1 | 50 |
| Compound 67 | 30 | 14 | 35.7 | 27.0 | +16.2 | 50 |
| Virus control |  | 14 | 71.4 | 10.8 |  |  |
| Compound 75 | 30 | 14 | 35.7 | 27.3 | +14.3 | 50 |
| Compound 29 | 30 | 14 | 35.7 | 26.7 | +13.7 | 50 |
| Compound 2 | 30 | 14 | 42.9 | 22.4 | +9.5 | 40 |
| Virus control |  | 14 | 71.4 | 13.0 |  |  |
| Compound 32 | 30 | 14 | 42.9 | 22.2 | +10.0 | 33 |
| Compound 44 | 30 | 14 | 28.6 | 32.3 | +20.1 | 55 |
| Compound 71 | 30 | 14 | 35.7 | 28.6 | +16.4 | 44 |
| Virus control |  | 14 | 64.3 | 12.2 |  |  |

Example 12

Antiviral Action of the Compounds of General Formula (I) Against Mouse-Adapted RS Virus Antiviral efficiency of chemical compounds against RSV in experimental mouse model in vivo was determined for human virus hRSV that was previously adapted to the growth in mouse lungs. The animals were infected with the virus at a dose of 5.0 logTCID$_{50}$ intranasally under brief ether anesthesia in a volume of 0.05 ml/mouse. The tested compounds were administered orally once daily for 5 days according to the treatment scheme at a dose of 30 mg/kg. The first administration was performed at 24 hours after infection. The placebo administered to mice consisted of a saline solution. Intact animals served as a negative control were hold under the same conditions as the experimental animals, in separate rooms. Experimental groups comprised 12 animals. Ribavirin at dose of 40 mg/kg was used as a reference preparation.

The antiviral activity of the tested compounds was determined by the efficiency for the prevention of a weight loss and by the suppression of the reproduction of hRSV in the

TABLE 7

Average body weight of the mice on days 5 and 7 after infection

| Preparation | Body weight of the mice on days 5 and 7 after infection with hRSV (M ± SD), n = 6 | |
|---|---|---|
|  | Day 5 | Day 7 |
| Compound 1 | 16.43 ± 0.14# | 17.98 ± 0.26# |
| Compound 117 | 16.07 ± 0.12# | 16.48 ± 0.28# |
| Compound 3 | 16.65 ± 0.28# | 17.32 ± 0.25# |
| Compound 120 | 16.12 ± 0.27# | 17.22 ± 0.20# |
| Compound 4 | 16.77 ± 0.20 | 17.08 ± 0.32# |
| Compound 5 | 16.02 ± 0.16# | 17.78 ± 0.26# |
| Compound 121 | 16.35 ± 0.20# | 17.38 ± 0.29# |
| Compound 122 | 16.93 ± 0.32 | 16.37 ± 0.21# |
| Compound 123 | 15.87 ± 0.20# | 17.55 ± 0.53 |
| Compound 124 | 16.43 ± 0.26# | 16.37 ± 0.43# |
| Compound 6 | 16.47 ± 0.26# | 17.02 ± 0.29# |
| Compound 7 | 17.17 ± 0.26# | 18.53 ± 0.55 |
| Compound 8 | 15.18 ± 0.18 | 17.13 ± 0.27# |
| Compound 9 | 15.75 ± 0.33 | 16.18 ± 0.29# |
| Compound 10 | 16.18 ± 0.29# | 16.53 ± 0.20# |
| Ribavirin | 16.20 ± 0.24# | 17.23 ± 0.22# |
| Virus control | 15.45 ± 0.25 | 15.32 ± 0.31 |
| Intact | 17.30 ± 0.19# | 18.00 ± 0.24# | statistically significant differences vs. the control animals (t-criterion, p < 0.05).

In addition, the therapeutic action of the compounds of general formula (I) was evaluated by their ability to suppress the reproduction of hRSV virus in the mouse lungs on days 5 and 7 after infection. A viral titer was determined by the titration of a 10% suspension of lungs in Hep-2 cell culture. The result was recorded at 2 days after incubation at 37° C. by TCID. The results of the determination of the infectious activity of hRSV in the mouse lung suspensions in Hep-2 cell culture after administration of the tested compounds and the reference preparation are given in Table 8. The administration of the compounds of general formula I to the animals led to a reduction in the hRSV infectious activity.

The study of antiviral activity of the compounds of general formula (I) in mouse hRSV infection model showed that the claimed compounds prevented a weight loss and reduced the virus reproduction in the lungs of the animals.

TABLE 8

Suppression of the reproduction of hRSV virus in mouse lungs

| Preparation | Day 5 | | Day 7 | |
| --- | --- | --- | --- | --- |
| | lg | Δlg | lg | Δlg |
| Compound 1 | 2.88 ± 0.59 | 1.73 ± 0.59 | 1.46 ± 0.17 | 2.34 ± 0.17 |
| Compound 117 | 3.00 ± 0.41 | 1.60 ± 0.41 | 1.46 ± 0.24 | 2.22 ± 0.34 |
| Compound 3 | 3.04 ± 0.42 | 1.56 ± 0.42 | 1.46 ± 0.17 | 2.18 ± 0.28 |
| Compound 120 | 3.04 ± 0.47 | 1.56 ± 0.47 | 1.50 ± 0.25 | 2.05 ± 0.25 |
| Compound 4 | 2.58 ± 0.51 | 2.02 ± 0.51 | 1.38 ± 0.24 | 2.58 ± 0.53 |
| Compound 5 | 2.17 ± 0.37 | 2.43 ± 0.37 | 0.88 ± 0.31 | 2.93 ± 0.31 |
| Compound 121 | 3.08 ± 0.47 | 1.52 ± 0.47 | 1.50 ± 0.14 | 2.09 ± 0.22 |
| Compound 122 | 3.04 ± 0.44 | 1.56 ± 0.44 | 1.75 ± 0.41 | 1.88 ± 0.47 |
| Compound 123 | 2.50 ± 0.43 | 2.10 ± 0.43 | 1.33 ± 0.19 | 2.62 ± 0.50 |
| Compound 124 | 2.46 ± 0.22 | 2.14 ± 0.22 | 0.83 ± 0.37 | 2.97 ± 0.37 |
| Ribavirin | 2.1 ± 0.12 | 2.4 ± 0.12 | 1.15 ± 0.12 | 2.4 ± 0.12 |
| Virus control | 4.60 ± 0.30 | | 3.8 ± 0.29 | |

* statistically significant differences vs. the control animals (t-criterion, $p < 0.05$).

Example 13

Antiviral Action of the Compounds of General Formula (I) Against RS Virus in a Model of Mice with a Suppressed Immune System.

Antiviral activity of the chemical compounds against human respiratory syncytial virus (strain A2, ATCC VR-1540 with an infectious titer of $5 \times 10^6$ TCID$_{50}$/ml) was assessed in a viral pneumonia model in Balb/c mice. The virus was inoculated to animals intranasally in a volume of 50 μl under brief ether anesthesia. To suppress an immune response to RS virus, animals were abdominally administered cyclophosphan at a dose of 100 mg/kg 5 days before infection. The tested compounds were administered according to the treatment scheme once daily at a dose of 30 mg/kg for 5 days, starting at 24 hours after infection. The activity of the compounds was assessed by a reduction in edema of the lungs infected with respiratory syncytial virus compared to the control, on day 5 after infection.

The results represented in Table 9 for some particular compounds of general formula (I) (without any limitation to the recited compounds) show that infection of the animals with the virus led to the formation of severe pulmonary edema (3.15-2.05 score from possible 4). The used compounds of general formula (I) had a normalizing action on the structure of the lung tissue.

TABLE 9

The degree of edema in RS-viral pneumonia in Balb/c mice on day 5 after infection under conditions of administration of the tested compounds and the reference preparation (M ± SD, n = 5)

| Tested compounds and reference preparation | Dose, mg/kg | Degree of pulmonary edema on day 5 after infection, score |
| --- | --- | --- |
| Virus control | — | 3.15 ± 0.22 |
| Compound 3 | 30 | 1.6 ± 0.89* |
| Compound 1 | 30 | 1.3 ± 0.27 |
| Ribavirin | 50 | 1.75 ± 0.59* |
| Virus control | — | 2.70 ± 0.25 |
| Compound 5 | 30 | 1.10 ± 0.19* |
| Compound 6 | 30 | 0.90 ± 0.22* |
| Compound 4 | 30 | 1.95 ± 0.31 |
| Compound 9 | 30 | 1.00 ± 0.17* |
| Ribavirin | 50 | 1.00 ± 0.17* |
| Virus control | — | 2.05 ± 0.23 |
| Compound 120 | 30 | 1.05 ± 0.14* |
| Compound 121 | 30 | 0.90 ± 0.21* |
| Compound 123 | 30 | 1.30 ± 0.17* |
| Ribavirin | 50 | 1.24 ± 0.18* |

*marked values were different from the control values according to t-criterion ($p < 0.05$).

Example 14

Antiviral Activity of the Compounds of Formula (I) Against Fhinovirus

The study was performed by using author's hRV strain deposited in the State Collection of viruses (GKV) (reg. No. 2730). The animals were infected with the virus intranasally under brief ether anesthesia in a volume of 0.05 ml/mouse.

The virus was previously titrated in mice to determine the efficiency of the compounds against hRV in an in vivo experimental model, then the mice were infected, and the preparation was administered orally. On days 2, 3 and 4 after infection, an infectious titer was assessed by titration of a lung suspension in Hela cell culture.

The studied compounds and placebo (saline solution) were orally administered to the mice once daily for 5 days, starting 12 hours after induction. The compounds were administered at a dose of 30 mg/kg of body weight. Ten intact animals that were kept under the same conditions as experimental animals in a separate room served as a negative control.

The antiviral activity of the tested compounds was evaluated on days 2, 3 and 4 after infection by the dynamics of weight changes of the body and lungs in mice and by a reduction of the virus infectious activity determined in Hela cell culture. The infectious titer of RV virus in the lungs of the experimental group, compared to the titer in the control group, was determined by TCID. A criterion of the antiviral efficiency of the preparations was a difference between titers in the control (without preparation) and experimental groups expressed in logarithm units—Δ1 g TCID$_{50}$. The difference was calculated according to the formula: (log A)–(log B).

Results of measuring the animal weight for some particular compounds of formula (I) (without any limitation to the recited compounds) are represented in the table 10.

TABLE 10

Body weight of the mice after infection with hRV

| Preparation | Dose (mg/kg) | Day after infection | | | | |
|---|---|---|---|---|---|---|
| | | 0 | 1 | 2 | 3 | 4 |
| Compound 4 | 30 | 7.77 ± 1.02 | 7.27 ± 1.27# | 12.66 ± 2.32# | 13.14 ± 1.5*# | 13.23 ± 1.38* |
| Compound 1 | 30 | 7.36 ± 0.97 | 8.2 ± 4.25# | 13.03 ± 3.51# | 13.47 ± 1.36* | 13.99 ± 1.53* |
| Ribavirin | 40 | 7.66 ± 0.89 | 8.81 ± 5.94# | 13.87 ± 5.11* | 13.11 ± 1.37# | 13.37 ± 1.22* |
| Intact | | 7.52 ± 0.05 | 8.41 ± 0.84* | 13.63 ± 1.22* | 14.33 ± 1.23* | 14.48 ± 0.9* |
| Virus control | | 7.72 ± 0.98 | 7.54 ± 0.89# | 12.57 ± 1.58# | 12.63 ± 1.13# | 12.39 ± 0.72# | statistically significant differences vs the intact animals (t-criterion, $p < 0.05$);
*statistically significant differences vs. the control animals (t-criterion, $p < 0.05$).

The development of the infectious process was associated with a reduction in the body weight of the animals in the virus control group, wherein the body weight of the mice treated with the tested compounds of general formula (I) was statistically significantly different from the body weight of the control animals on days 3 and 4.

The study of the lung weight of the mice in rhinovirus infection and the therapeutic scheme of administration of the preparations showed that during the experiment, the lung weight of the infected mice exceeded the lung weight of the intact mice, indicating an active infectious process. On day 4, the lung weight of the mice being under the effect of the studied preparations was significantly different from the virus control group and was almost the same as the lung weight of the intact animals. Data of some particular compounds (without any limitation to the recited compounds) are represented in Table 11.

The treatment with the compounds of general formula (I) resulted to a reduction in hRV infectious activity on days 3 and 4 after infection.

The study of the antiviral activity of the compounds of general formula (I) in mouse hRV infection model showed that the claimed compounds prevented a weight loss and an increase in the lung weight to the values observed in the group of intact animals and reduces the virus reproduction in the animal lungs.

Example 15

Antiviral Activity of the Compounds of Formula (I) Against Influenza Virus.

The study was conducted by using influenza virus strain A/California/07/09 (H1N1) pdm09. White outbred female

TABLE 11

Lung weight of the mice after infection with hRV

| Preparation | Dose (mg/kg) | Day after infection | | |
|---|---|---|---|---|
| | | 2 | 3 | 4 |
| Compound 4 | 30 | 142 ± 4.81*# | 135.9 ± 4.18*# | 134.2 ± 3.68*# |
| Compound 1 | 30 | 136.9 ± 5.93*# | 140.8 ± 5.14*# | 128.2 ± 5.81* |
| Ribavirin | 40 | 152.6 ± 4.55# | 130.1 ± 5.4*# | 120.5 ± 3.37* |
| Intact | | 120.2 ± 2.39* | 123.7 ± 2.75* | 125.3 ± 3.65* |
| Virus control | | 153.8 ± 3.55# | 167.8 ± 4.16# | 183.5 ± 3.03# | statistically significant differences vs. the intact animals (t-criterion, $p < 0.05$);
*statistically significant differences vs. the control animals (t-criterion, $p < 0.05$).

Results of the determination of hRV infectious activity in suspensions of the mouse lungs in Hela cell culture after administration of some particular compounds of general formula (I) (without any limitation to the recited compounds) are represented in Table 12.

mice used in the experiment weighing 14-16 g were divided to groups by 20 animals.

During the experiment, each animal was observed every day. The observation included the assessment of the general behavior and body condition of the animals. In days of

TABLE 12

Suppression of the reproduction of hRV virus in mouse lungs

| Preparation | Dose of preparation, mg/kg | Infectious titer of the virus in lungs, lg $TCID_{50}$ Day 2 after infection | Suppression of the reproduction of the virus in mouse lungs, Δ lg | Infectious titer of the virus in lungs, lg $TCID_{50}$ Day 3 after infection | Suppression of the reproduction of the virus in mouse lungs | Infectious titer of the virus in lungs, lg $TCID_{50}$ Day 4 after infection | Suppression of the reproduction of the virus in mouse lungs |
|---|---|---|---|---|---|---|---|
| | | lg | Δ lg | lg | Δ lg | lg | Δ lg |
| Compound 1 | 30 | 2.9 ± 0.49 | 1.1 ± 0.49 | 0.8 ± 0.31 | 1.7 ± 0.31 | 0.03 ± 0.08 | 2.18 ± 0.08 |
| Compound 4 | 30 | 2.35 ± 0.65 | 1.65 ± 0.65 | 0.6 ± 0.27 | 1.9 ± 0.27 | 0 ± 0 | 2.2 ± 4.68 |
| Ribavirin | 40 | 3.13 ± 0.5 | 0.88 ± 0.5 | 0.33 ± 0.26 | 2.18 ± 0.26 | 0.2 ± 0.16 | 2 ± 0.16 |
| Control | | 4.03 ± 0.38 | | 2.5 ± 0.2 | | 2.18 ± 0.31 | | administration of preparations, the observation was conducted before administration of a preparation in a certain time and at about two hours after administration. The animals were handled according to the International Standards.

The mice were infected with influenza virus A/California/07/09 (H1N1) pdm09 intranasally in a volume of 0.05 ml comprising 5 LD50.

The therapeutic effect of the compounds of general formula (I) was studied by oral administration of the compounds to the infected mice once daily at a dose of 30 mg/kg/mouse at 24, 48, 72, 96, and 120 hours after infection with the virus. Mice of the control group were administered placebo under the same conditions (0.2 ml of a saline solution). The animals were monitored for 14 days after infection and fatal cases caused by influenza pneumonia in the treated and control groups were registered. The specificity of animal death from influenza pneumonia was supported by the registration of anatomo-pathological changes in the lungs of dead animals.

The activity of the compounds was evaluated by comparison of the mortality rates between the groups of animals administered a preparation and placebo.

The expectancy life of the infected animals administered placebo was 7.2±2.2 days at a mortality rate of 95%.

The mortality rate of the groups of animals administered the compounds of general formula (I) was reduced by 30-60% and the expectancy life was higher than in the control mice. Data for some particular compounds of general formula (I) (without any limitation to the recited compounds) are represented in table 13.

TABLE 13

Mortality rate in experimental groups of animals

| No | Preparation | Dose (mg/ml) | Mortality rate, % |
|----|-------------|--------------|-------------------|
| 1  | Compound 1 (KhS-8) | 30 | 35.0 |
| 2  | Compound 5 (KhS-221-GI) | 30 | 45.0 |
| 3  | Compound 4 (KhS-217) | 30 | 65.0 |
| 4  | Compound 12 | 30 | 60.0 |
| 5  | Compound 20 | 30 | 50.0 |
| 6  | Compound 23 | 30 | 40.0 |
| 7  | Compound 24 | 30 | 55.0 |
| 8  | Compound 30 | 30 | 50.0 |
| 9  | Compound 35 | 30 | 55.0 |
| 10 | Compound 36 | 30 | 60.0 |
| 11 | Compound 83 | 30 | 45.0 |
| 12 | Virus control |  | 95.0 |
| 13 | Intact |  | 0.0 |

Example 16

Dosage Forms of the Compounds According to the Invention

The compounds according to the invention may be administered orally, intramuscularly or intravenously in a unit dosage form comprising non-toxic pharmaceutically acceptable carriers.

The compounds may be administered to a patient in daily doses of from 0.1 to 10 mg/kg of body weight, preferably in doses of from 0.5 to 5 mg/kg, one or more times a day.

In addition it should be noted that a particular dose for a particular patient depends on many factors, including the activity of a certain compound, patient's age, body weight, gender, general health condition and diet, the time and route of administration of a pharmaceutical agent and the rate of its excretion from the body, a specific combination of drugs and the severity of a disease in an individual to be treated.

The pharmaceutical compositions according to the present invention comprise a compound of general formula (I) in an amount effective to achieve a desired technical result, and can be administered in a unite dosage form (for example, in a solid, semi-solid, or liquid form) comprising the compounds according to the present invention as an active agent in a mixture with a carrier or an excipient suitable for intramuscular, intravenous, oral and sublingual administration, administration by inhalation, intranasal and intrarectal administration. The active ingredient can be in a composition together with conventional nontoxic pharmaceutically acceptable carriers suitable for the manufacture of solutions, tablets, pills, capsules, coated pills, emulsions, suspensions, ointments, gels, and any other dosage forms.

As an excipient, various compounds can be used, such as saccharides, for example, glucose, lactose, of sucrose; mannitol or sorbitol; cellulose derivatives; and/or calcium phosphates, for example, tricalcium phosphate or calcium hydrophosphate. As a binder, the following compounds can be used, such as a starch paste (for example, corn, wheat, rice, or potato starch), gelatin, tragacanth, methylcellulose, hydroxypropylmethylcellulose, sodium carboxymethylcellulose, and/or polyvinylpyrrolidone. Optionally used disintegrants are the above-mentioned starches and carboxymethylstarch, crosslinked polyvinylpyrrolidone, agar-agar, or alginic acid or a salt thereof, such as sodium alginate.

Additives that can be optionally used are flowability-control agents and lubricants, such as silicon dioxide, talc, stearic acid and salts thereof, such as magnesium stearate or calcium stearate, and/or propylene glycol.

In preparing a unit dosage form, the amount of an active agent used in combination with a carrier can vary depending on a recipient to be treated and on a particular route of administration of a therapeutic agent.

For example, when the compounds according to the present invention are used in the form of a solution for injection, the amount of the active agent in this solution is up to 5 wt. %. A diluent may be selected from a 0.9% sodium chloride solution, distilled water, a Novocain solution for injection, Ringer's solution, a glucose solution, and specific solubilizing adjuvants. When the compounds according to the present invention are administered in tablet form, their amount is from 5.0 to 500 mg per unit dosage form.

Dosage forms according to the present invention are prepared by conventional procedures, such as blending, granulation, forming coating pills, dissolution, and lyophilization.

Tableted Form

A tableted form is prepared by using the following ingredients:

| Active agent: | | | |
|---|---|---|---|
| Compound according to the invention or a pharmaceutically acceptable salt thereof | 2.00 mg | 10 mg | 100 mg |
| Additives: | | | |
| Microcrystalline cellulose, MCC 102 (USP, Ph. Eur.); | 47.70 mg | 70.55 mg | 95.90 mg |
| Lactose monohydrate (USP, Ph. Eur.); | 49.00 mg | 67.50 mg | 99.00 mg |
| Sodium starch glycolate (USP, Ph. Eur.); | 0.50 mg | 0.75 mg | 1.50 mg |
| Talc (USP, Ph. Eur.); | 0.40 mg | 0.60 mg | 1.20 mg |

| | | | |
|---|---|---|---|
| Magnesium stearate (USP, Ph. Eur.) | 0.40 mg | 0.60 mg | 2.40 mg |
| Weight of the tablet core | 100.00 mg | 150.00 mg | 300.00 mg |
| Coating (USP, Ph. Eur.) | 3.00 mg | 4.50 mg | 9.00 mg |
| Tablet weight | 103.00 mg | 154.50 mg | 309.00 mg |

The components are mixed and compressed to form tablets.

Suppositories

Example of the suppository composition

| | |
|---|---|
| Compound according to the invention or a pharmaceutically acceptable salt thereof | 1-100 mg |
| Cacao oil | amount required to prepare a suppository |

If necessary, rectal, vaginal, and urethral suppositories are prepared by using corresponding excipients.

Solution for Injection

Example of the composition of a solution for injections:

| | |
|---|---|
| Compound according to the invention or a pharmaceutically acceptable salt thereof | 1-50 mg |
| Water for injection | 2 ml |

What is claimed is:

1. A compound having the following formula:

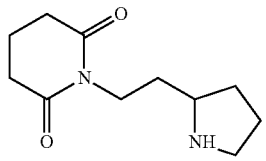 [SMILES: O=C1CCCC(=O)N1CCC1CCCN1]

or a pharmaceutically acceptable salt thereof.

2. A medicament for treatment of a respiratory tract disease, which is a compound or a pharmaceutically acceptable salt thereof of claim 1.

3. The medicament of claim 2, wherein the respiratory tract disease is rhinosinusitis.

4. The medicament of claim 2, wherein the respiratory tract disease is caused by an RNA-comprising virus.

5. The medicament of claim 4, wherein the RNA-comprising virus is selected from the group consisting of rhinovirus, Coxsackie virus, and influenza virus.

6. The medicament of claim 2, wherein the respiratory tract disease is exacerbations of asthma, chronic obstructive pulmonary disease, bronchitis and mucoviscidosis, which are caused by rhinovirus, influenza virus and/or respiratory syncytial virus.

7. A pharmaceutical composition for treatment of a respiratory tract disease, comprising an effective amount of a compound or a pharmaceutically acceptable salt thereof of claim 1, and a pharmaceutically acceptable carrier.

8. The pharmaceutical composition of claim 7, wherein the respiratory tract disease is rhinosinusitis.

9. The pharmaceutical composition of claim 7, wherein the respiratory tract disease is caused by an RNA-comprising virus.

10. The pharmaceutical composition of claim 9, wherein the RNA-comprising virus is selected from the group consisting of rhinovirus, Coxsackie virus, and influenza.

11. The pharmaceutical composition of claim 7, wherein the respiratory tract disease is exacerbations of asthma, chronic obstructive pulmonary disease, bronchitis and mucoviscidosis, which are caused by rhinovirus, influenza virus and/or respiratory syncytial virus.

12. A method of treating a respiratory tract disease caused by an RNA-comprising virus or being rhinosinusitis, comprising administering to a patient an effective amount of a compound or a pharmaceutically acceptable salt thereof of claim 1.

13. The method of claim 12, wherein the respiratory tract disease is rhinosinusitis.

14. The method of claim 12, wherein the respiratory tract disease is caused by an RNA-comprising virus.

15. The method of claim 14, wherein the RNA-comprising virus is selected from the group consisting of rhinovirus, Coxsackie virus, and influenza virus.

16. The method of claim 12, wherein the respiratory tract disease is exacerbations of asthma, chronic obstructive pulmonary disease, bronchitis and mucoviscidosis, which are caused by rhinovirus, influenza virus and/or respiratory syncytial virus.

* * * * *

UNITED STATES PATENT AND TRADEMARK OFFICE
CERTIFICATE OF CORRECTION

PATENT NO. : 10,377,739 B2  
APPLICATION NO. : 16/192065  
DATED : August 13, 2019  
INVENTOR(S) : Vladimir Evgenievich Nebolsin et al.

Page 1 of 1

It is certified that error appears in the above-identified patent and that said Letters Patent is hereby corrected as shown below:

On the Title Page

Under Abstract, Item (57):
Please delete:

"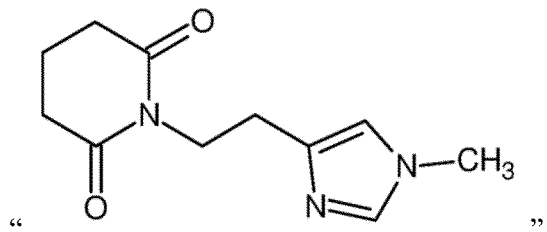"

And insert:

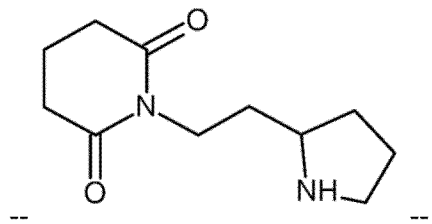

-- --

Signed and Sealed this  
Thirty-first Day of December, 2019

Andrei Iancu  
*Director of the United States Patent and Trademark Office*